(12) United States Patent
Suh et al.

(10) Patent No.: US 11,969,728 B2
(45) Date of Patent: Apr. 30, 2024

(54) MICROFLUIDIC DEVICE MIMICKING A BIOLOGICAL MICROENVIRONMENT AND COMPRISING DIFFUSION CHAMBERS AND CHANNELS

(71) Applicant: KOREA INSTITUTE OF SCIENCE AND TECHNOLOGY, Seoul (KR)

(72) Inventors: Seung Beum Suh, Seoul (KR); Sunghyun Cho, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 703 days.

(21) Appl. No.: 17/086,462

(22) Filed: Nov. 2, 2020

(65) Prior Publication Data
US 2021/0316302 A1    Oct. 14, 2021

(30) Foreign Application Priority Data

Apr. 14, 2020   (KR) .................. 10-2020-0045375

(51) Int. Cl.
| | |
|---|---|
| *B01L 3/00* | (2006.01) |
| *C12M 3/06* | (2006.01) |
| *G01N 33/50* | (2006.01) |

(52) U.S. Cl.
CPC ....... *B01L 3/502715* (2013.01); *C12M 23/16* (2013.01); *G01N 33/5008* (2013.01);
(Continued)

(58) Field of Classification Search
CPC ......... B01L 3/502715; B01L 3/502746; B01L 3/502761; B01L 2200/0694;
(Continued)

(56) References Cited

U.S. PATENT DOCUMENTS

| | | | |
|---|---|---|---|
| 2006/0140051 A1 | 6/2006 | Kim et al. | |
| 2011/0306041 A1* | 12/2011 | Viovy | C12N 5/0619 |
| | | | 435/7.1 |

(Continued)

FOREIGN PATENT DOCUMENTS

| | | |
|---|---|---|
| KR | 1020060057093 A | 5/2006 |
| KR | 10-2008-0093225 A | 10/2008 |

(Continued)

OTHER PUBLICATIONS

Agua Sobrino et al., "3D microtumors in vitro supported by perfused vascular networks," Scientific Reports, 2016, pp. 1-11, vol. 6.

(Continued)

*Primary Examiner* — Michael L Hobbs
(74) *Attorney, Agent, or Firm* — CANTOR COLBURN LLP

(57) ABSTRACT

The present disclosure relates to a microfluidic device capable of mimicking a biological microenvironment thereby achieving control of a microenvironment with time through control of the diffusion of target elements between chambers by interrupting or generating fluid flow inside a channel, and a method for manufacturing the same, and the microfluidic device according to an aspect of the present disclosure can mimic the biological microenvironment which changes constantly with time via a simple temporary operation of generating or interrupting fluid flow in the channel mechanically and can control diffusion via a simple method, and accordingly, a complicated microenvironment can be reproduced since the number and arrangement of diffusion chambers and channels can be designed variously.

17 Claims, 16 Drawing Sheets

(52) U.S. Cl.
CPC ... *B01L 2200/0694* (2013.01); *B01L 2200/12* (2013.01); *B01L 2300/0861* (2013.01); *B01L 2400/0472* (2013.01)

(58) Field of Classification Search
CPC ......... B01L 2200/0652; B01L 2200/12; B01L 2300/0861; B01L 2300/069; C12M 23/16; C12M 41/00; G01N 33/5011; G01N 33/5029; G01N 33/5082
See application file for complete search history.

(56) References Cited

U.S. PATENT DOCUMENTS

| | | | |
|---|---|---|---|
| 2015/0299631 | A1* | 10/2015 | Prabhakarpandian ..................... C12M 21/08 435/29 |
| 2020/0086319 | A1 | 3/2020 | Gilbert et al. |

FOREIGN PATENT DOCUMENTS

| | | |
|---|---|---|
| KR | 10-2010-0018505 A | 2/2010 |
| KR | 10-2016-0005279 A | 1/2016 |
| KR | 101741815 B1 | 6/2017 |
| WO | 2008/124781 A1 | 10/2008 |

OTHER PUBLICATIONS

Alexandra Sontheimer-Phelps et al., "Modelling cancer in microfluidic human organs-on-chips," Nat. Rev. Cancer, 2019, pp. 65-81, vol. 19, No. 2.
Barbara Muz et al., "The role of hypoxia in cancer progression, angiogenesis, metastasis, and resistance to therapy," Hypoxia, 2015, pp. 83-92.
Boyang Zhang et al., "Advances in organ-on-a-chip engineering," Nat. Rev. Materials, 2018, pp. 257-278, vol. 3, No. 8.
C. L. Chaffer et al., "A perspective on cancer cell metastasis," Science, 2011, pp. 1559-1564, vol. 331.
D. Huh et al., "Reconstituting organ-level lung functions on a chip," Science, Jun. 2010, pp. 1662-1668, vol. 328.
D. Ribatti et al., "The history of the angiogenic switch concept," Leukemia, 2007, pp. 44-52, vol. 21, No. 1.
Dongeun Huh et al., "Acoustically detectable cellular-level lung injury induced by fluid mechanical stresses in microfluidic airway systems," PNAS, Nov. 27, 2007, pp. 18886-18891, vol. 104, No. 48.
Duc-Huy T. Nguyen et al., "Biomimetic model to reconstitute angiogenic sprouting morphogenesis in vitro," PNAS, 2013, pp. 6712-6717, vol. 110, No. 17.
F. R. Balkwill et al., "The tumor microenvironment at a glance," J. Cell Sci., 2012, pp. 5591-5596, vol. 125, No. 23.
G. Bergers et al., "Tumorigenesis and the angiogenic switch," Nat. Rev. Cancer, 2003, pp. 401-410, vol. 3, No. 6, Nature Publishing Group.
Hojeong Jeon et al., "Quantitative analysis of single bacterial chemotaxis using a linear concentration gradient microchannel," Biomedical Microdevices, 2009, pp. 1135-1143, vol. 11.
Judah Folkman, "Tumor Angiogenesis," Adv. Cancer Res., 1985, pp. 175-203, vol. 43.
M. Wilkinson, "The Potential of Organ on Chip Technology for Replacing Animal Testing," in Animal Experimentation: Working Towards a Paradigm Change, 2019, pp. 639-653.
Maonan Wang et al., "Role of tumor microenvironment in tumorigenesis," J. Cancer, 2017, pp. 761-773, vol. 8, No. 5.
Min Huang et al., "Molecularly targeted cancer therapy: Some lessons from the past decade," Trends Pharmacol. Sci., 2014, vol. 35, No. 1, pp. 41-50.
Neil S. Forbes, "Engineering the perfect (bacterial) cancer therapy," Nat. Rev. Cancer, 2010, pp. 785-794, vol. 10, No. 11.
S. J. Hachey et al., "Applications of tumor chip technology," Lab Chip, 2018, pp. 2893-2912, vol. 18, No. 19, The Royal Society of Chemistry.
S. N. Bhatia et al., "Microfluidic organs-on-chips," Nat. Biotechnol., 2014, pp. 760-772, vol. 32, No. 8.
Steven A. Rosenberg, "Decade in review—cancer immunotherapy: Entering the mainstream of cancer treatment," Nat. Rev. Clin. Oncol., 2014, 2 pages, vol. 11, Macmillan Publishers Limited.
Ting-Hsiang Wu et al., "Pulsed laser triggered high speed microfluidic fluorescence activated cell sorter," Lap Chip, 2012, pp. 1378-1383, Vo. 12, No. 7, The Royal Society of Chemistry.
Ting-Hsiang Wu et al., "Pulsed laser triggered high speed microfluidic switch," Applied Physics Letters, 2008, vol. 93, No. 144102.
Yao Yuan et al., "Role of the tumor microenvironment in tumor progression and the clinical applications (Review)," Oncol. Rep., 2016, pp. 2499-2515, vol. 35, No. 5.
Hyungseok Choi et al., "Tumor-on-a-chip: Multiple Cell Interacting Model with Diffusion Switching System," Oct. 16, 2019, The 4th International Conference on Active Materials and Soft Mechatronics.

* cited by examiner

MICROFLUIDIC DEVICE MIMICKING A BIOLOGICAL MICROENVIRONMENT AND COMPRISING DIFFUSION CHAMBERS AND CHANNELS

CROSS-REFERENCE TO RELATED APPLICATION

This application claims priority to Korean Patent Application No. 10-2020-0045375, filed on Apr. 14, 2020, and all the benefits accruing therefrom under 35 U.S.C. § 119, the contents of which in its entirety are herein incorporated by reference.

BACKGROUND

1. Field

The present disclosure discloses a microfluidic device capable of mimicking a biological microenvironment by interrupting or generating fluid flow inside a channel, thereby achieving control of a microenvironment with time through control of the diffusion of target elements between chambers, a method for manufacturing the same, a method for controlling a microenvironment in real time using the same, and a method for measuring and observing cellular response using the same.

2. Description of the Related Art

Cancer is a disease which is the major cause of death globally. Many researchers have studied cancer systems in order to develop effective therapeutic methods in addition to the existing surgery, chemotherapy and radiation therapy. Various cancer therapies have been studied and promising results have been proposed such as molecularly targeted therapy (M. Huang, A. Shen, J. Ding, and M. Geng, "Molecularly targeted cancer therapy: Some lessons from the past decade," Trends Pharmacol. Sci., vol. 35, no. 1, pp. 41-50, 2014), immunotherapy (S. A. Rosenberg, "Decade in review—cancer immunotherapy: Entering the mainstream of cancer treatment," Nat. Rev. Clin. Oncol., 2014), etc. However, there have been little successful application to medical treatment. The major obstacle to commercialization is that immense cost and time are needed for verification of the proposed system and drug development. On average, 2.6 billion dollars is spent for 12 years for 5 stages of clinical trials until new drug development is completed, and about 90% or more of candidate drugs that have passed preclinical animal tests fail to proceed to the market (M. Wilkinson, "The Potential of Organ on Chip Technology for Replacing Animal Testing," in Animal Experimentation: Working Towards a Paradigm Change, 2019). It is because the animal model cannot accurately represent the human model and inaccurate tumor targeting and tissue infiltration occur during clinical trials, which require additional cost and time (N. S. Forbes, "Engineering the perfect (bacterial) cancer therapy," Nat. Rev. Cancer, vol. 10, no. 11, pp. 785-794, 2010). Considering that clinical trials are essential and irreplaceable procedures, it is the best approach to simplify the preclinical phases very precisely in order to reduce the cost and time of drug development.

In order to reduce the cost of new cancer therapy development, microfluidics-based chips (organs-on-chips) that provide high-throughput and fast drug screening abilities in preclinical phases have been studied for decades (B. Zhang, A. Korolj, B. F. L. Lai, and M. Radisic, "Advances in organ-on-a-chip engineering," Nat. Rev. Mater., vol. 3, no. 8, pp. 257-278, 2018; S. N. Bhatia and D. E. Ingber, "Microfluidic organs-on-chips," Nat. Biotechnol., vol. 32, no. 8, pp. 760-772, 2014; A. Sontheimer-Phelps, B. A. Hassell, and D. E. Ingber, "Modelling cancer in microfluidic human organs-on-chips," Nat. Rev. Cancer, vol. 19, no. 2, pp. 65-81, 2019). The main advantage of using a microfluidic chip in vitro is that the delicate physiological functions and pathological processes in vivo can be reproduced and, through this, meaningful preclinical data can be provided prior to clinical trials (S. N. Bhatia and D. E. Ingber, "Microfluidic organs-on-chips," Nat. Biotechnol., vol. 32, no. 8, pp. 760-772, 2014; A. Sontheimer-Phelps, B. A. Hassell, and D. E. Ingber, "Modelling cancer in microfluidic human organs-on-chips," Nat. Rev. Cancer, vol. 19, no. 2, pp. 65-81, 2019; S. J. Hachey and C. C. W. Hughes, "Applications of tumor chip technology," Lab Chip, vol. 18, no. 19, pp. 2893-2912, 2018). For example, a lung-on-a-chip which vibrates mechanically showed the same response to bacteria and cytokines, and it was also shown that physical vibrational stress improves absorption of nanoparticles by cells (D. Huh, B. D. Matthews, A. Mammoto, M. Montoya-Zavala, H. Yuan Hsin, and D. E. Ingber, "Reconstituting organ-level lung functions on a chip," Science (80-.), 2010). In addition, an in-vitro angiogenesis chip showed responses comparable to that of proangiogenic factors and antiangiogenic factors (A. Sobrino et al., "3D microtumors in vitro supported by perfused vascular networks," Sci. Rep., vol. 6, no. July, pp. 1-11, 2016).

The important aspect of an in-vitro tumor-on-a-chip, i.e., effectiveness, is determined by whether the chip similarly mimics the main features of an in-vivo tumor microenvironment (TME). During tumor growth, tumor cells recruit stromal cells, immune cells and vascular cells by secreting attractive molecules such as growth factors, chemokines and cytokine, and create a microenvironment in tissues (Y. Yuan, Y. C. Jiang, C. K. Sun, and Q. M. Chen, "Role of the tumor microenvironment in tumor progression and the clinical applications (Review)," Oncol. Rep., vol. 35, no. 5, pp. 2499-2515, 2016). When tumor cells being to interact with the recruited cells in the TME, the recruited cells help tumor growth by facilitating infiltration and metastasis, stimulating angiogenesis and maintaining proliferative signaling (M. Wang et al., "Role of tumor microenvironment in tumorigenesis," J. Cancer, vol. 8, no. 5, pp. 761-773, 2017). The TME has several main features that are distinguished from those of the normal cellular environment: 1) it allows tumor cells to interacts with nearby cells of various types, 2) the central regions of the tumor cells are in hypoxic states, 3) the environment is changed with time through angiogenesis, which is essential in specific tumor growth (M. Wang et al., "Role of tumor microenvironment in tumorigenesis," J. Cancer, vol. 8, no. 5, pp. 761-773, 2017; Y. Yuan, Y. C. Jiang, C. K. Sun, and Q. M. Chen, "Role of the tumor microenvironment in tumor progression and the clinical applications (Review)," Oncol. Rep., vol. 35, no. 5, pp. 2499-2515, 2016; F. R. Balkwill, M. Capasso, and T. Hagemann, "The tumor microenvironment at a glance," J. Cell Sci., vol. 125, no. 23, pp. 5591-5596, 2012).

Tumor angiogenesis is a distinct feature in tumor growth, and is very different from the normal physiological angiogenesis caused by unbalanced expression of proangiogenic factors such as vascular endothelial growth factor (VEGF) and antiangiogenic factors (G. Bergers and L. E. Benjamin, "Tumorigenesis and the angiogenic switch," Nat. Rev. Cancer, vol. 3, no. 6, pp. 401-410, 2003). When the "angiogenic switch" is turned on by a hypoxic state, proangiogenic factors are released excessively from the tumor cells and nearby cells around the tumor (e.g., macrophages, fibroblasts). As a result, endothelial cells are assembled toward the tumor and a new blood vessel is formed (D. Ribatti, B. Nico, E. Crivellato, A. M. Roccaro, and A. Vacca, "The history of the angiogenic switch concept," *Leukemia*, vol. 21, no. 1, pp. 44-52, 2007). This process is continued limitlessly as long as the tumor remains (J. Folkman, "Tumor Angiogenesis," *Adv. Cancer Res.*, 1985). Whereas a normally formed blood vessel is matured and stabilized quickly, this blood vessel has a permeable and abnormal vascular structure, and facilitates extravasation, circulation and relocation to new tissues, i.e., metastasis (G. Bergers and L. E. Benjamin, "Tumorigenesis and the angiogenic switch," *Nat. Rev. Cancer*, vol. 3, no. 6, pp. 401-410, 2003; B. Muz, P. de la Puente, F. Azab, and A. K. Azab, "The role of hypoxia in cancer progression, angiogenesis, metastasis, and resistance to therapy," *Hypoxia*, 2015; C. L. Chaffer and R. A. Weinberg, "A perspective on cancer cell metastasis," *Science.* 2011). It is evident that angiogenesis plays a critical role in the progression and spread of tumor. Researchers believe that better understanding of the role of angiogenesis in TME is valuable in developing a new and improved treatment strategy.

Accordingly, an effective tumor microenvironment chip (TME-on-a-chip) should reflect the change in TME including vascularization, hypoxic state and molecular exchange between cells. However, the existing chip mimicking angiogenesis in tumor cells (organ-on-a-chip) is limited in accurately reproducing the physiological phenomena occurring through interaction with a changing environment such as the on/off process of an angiogenic switch (A. Sobrino et al., "3D microtumors in vitro supported by perfused vascular networks," *Sci. Rep.*, vol. 6, no. July, pp. 1-11, 2016; D. H. T. Nguyen et al., "Biomimetic model to reconstitute angiogenic sprouting morphogenesis in vitro," *Proc. Natl. Acad. Sci. U.S.A.*, vol. 110, no. 17, pp. 6712-6717, 2013).

In addition, in order to embody a microenvironment changing with time on a microfluidic device via an on/off switching mechanism, there have been attempts to change the moving direction of a target element to be controlled by forming a bubble by irradiating a pulsed laser intentionally (Wu, Ting-Hsiang, et al., Pulsed laser triggered high speed microfluidic switch, *Applied Physics Letters*, 2008, 93.14: 144102), mimic a microenvironment with a valve device diverging to several directions by clamping interconnected tubes (Jeon, Hojeong, et al., Quantitative analysis of single bacterial chemotaxis using a linear concentration gradient microchannel, *Biomedical microdevices*, 2009, 11.5: 1135), or mimic a microenvironment by directly transferring desired fluids through two inlet channels and determining which fluid will be flown out of an outlet channel (Huh, Dongeun, et al., Acoustically detectable cellular-level lung injury induced by fluid mechanical stresses in microfluidic airway systems, *Proceedings of the National Academy of Sciences*, 2007 Nov. 27; 104(48): 18886-91). However, these methods are limited in embodying a microenvironment which is changed due to various factors because of the difficulty in realizing the methods, inefficiency in terms of time and cost due to additionally required devices, and complexity of configuration.

Therefore, the inventors of the present disclosure have designed and manufactured a simple variable microfluidic device (e.g., a tumor microenvironment chip) which is capable of controlling an in-vivo microenvironment, e.g., angiogenesis, with time by using a diffusion switch system.

SUMMARY

In an aspect, the present disclosure is directed to providing a microfluidic device mimicking a biological microenvironment, which includes: a plurality of diffusion chambers; and one or more channel disposed between the plurality of diffusion chambers, wherein the surface of the diffusion chamber and the channel is porous, and the diffusion of a target element between the plurality of diffusion chambers is controlled by interrupting or generating fluid flow inside the channel.

In another aspect, the present disclosure is directed to providing a method for manufacturing a microfluidic device mimicking a biological microenvironment, which includes: preparing a device-forming solution including a pre-polymer; forming a substrate by coating a scaffold solution including a polymer on a plate and forming a cavity in the substrate; and forming a microfluidic device by injecting the device-forming solution into the cavity formed in the substrate and curing the same.

In another aspect, the present disclosure is directed to providing a method for controlling a microenvironment in real time, which includes: interrupting or generating fluid flow inside one or more channel among the one or more channel of the microfluidic device mimicking a biological microenvironment described above.

In another aspect, the present disclosure is directed to providing a method for measuring and observing cellular response using a microfluidic device, which includes: loading a biological sample in one or more diffusion chamber among the one or more diffusion chamber of the plurality of diffusion chambers of the microfluidic device mimicking a biological microenvironment described above; and interrupting or generating fluid flow inside one or more channel among the one or more channel.

In an aspect, the present disclosure provides a microfluidic device mimicking a biological microenvironment, which includes: a plurality of diffusion chambers; and one or more channel disposed between the plurality of diffusion chambers, wherein the surface of the diffusion chamber and the channel is porous, and the diffusion of a target element between the plurality of diffusion chambers is controlled by interrupting or generating fluid flow inside the channel.

In another aspect, the present disclosure provides a method for manufacturing a microfluidic device mimicking a biological microenvironment, which includes: preparing a device-forming solution including a pre-polymer; forming a substrate by coating a scaffold solution including a polymer on a plate and forming a cavity in the substrate; and forming a microfluidic device by injecting the device-forming solution into the cavity formed in the substrate and curing the same.

In another aspect, the present disclosure provides a method for controlling a microenvironment in real time, which includes: interrupting or generating fluid flow inside one or more channel among the one or more channel of the microfluidic device mimicking a biological microenvironment described above.

In another aspect, the present disclosure provides a method for measuring and observing cellular response using a microfluidic device, which includes: loading a biological sample in one or more diffusion chamber among the one or more diffusion chamber of the plurality of diffusion chambers of the microfluidic device mimicking a biological microenvironment described above; and interrupting or generating fluid flow inside one or more channel among the one or more channel.

Since a microfluidic device 100 according to an aspect of the present disclosure includes a plurality of diffusion chambers 210, 220, 300 and one or more channel 410, 420 with the surface of which is porous, a diffusion path transporting a molecule, which is a target element, in a biological sample present in the diffusion chamber as signals can be provided. In addition, since the channel can control not only the diffusion of the target element passing therethrough but also the amount of the diffused target element (e.g., proangiogenic factor), it allows artificial manipulation of the change in the in-vivo microenvironment (e.g., angiogenic switch) in the microfluidic device. Accordingly, the microfluidic device according to an aspect of the present disclosure can mimic the biological microenvironment which changes constantly with time via a simple temporary operation of generating or interrupting fluid flow in the channel mechanically and can control diffusion via a simple method. Therefore, a complicated microenvironment can be reproduced since the number and arrangement of diffusion chambers and channels can be designed variously. Accordingly, the microfluidic device according to an aspect of the present disclosure can be utilized as a powerful tool for performing various biological evaluations in the field of medicine and biology.

BRIEF DESCRIPTION OF THE DRAWINGS

FIG. 3 shows, from left to right, a state where fluid flow inside channels 410, 420 is interrupted (no flow) and a diffusion switch is turned on such that the diffusion of a target element is started between diffusion chambers (a first side diffusion chamber 210, a central diffusion chamber 300 and a second side diffusion chamber 220) (diffusion switch on), a state where the diffusion switch is turned off such that interaction occurs between the diffusion chambers (the side diffusion chambers 210, 220 and the central diffusion chamber 300), a state where fluid flow is generated inside the channels 410, 420 (flow) and the diffusion switch is turned off such that the diffusion of the target element between the diffusion chambers (the side diffusion chambers 210, 220 and the central diffusion chamber 300) is interrupted (diffusion switch off), and a state where the diffusion switch is turned off such that the interaction between the diffusion chambers (the side diffusion chambers 210, 220 and the central diffusion chamber 300) is interrupted.

In FIG. 6, the light gray portion (corresponding to the portion represented by dots in FIG. 1 and FIG. 2A) represents channels and diffusion chambers, and the black portion (corresponding to the portion represented by black lines or white parts in FIG. 1 and FIG. 2A) represents a porous hydrogel.

In FIG. 7, the light gray portion represents FITC and the dark gray portion represents Cy5.

In FIG. 9, the white portion (corresponding to the portion represented by dots in FIG. 1 and FIG. 2A) represents channels and diffusion chambers, and the black portion (corresponding to the portion represented by black lines or white parts in FIG. 1 and FIG. 2A) represents a porous hydrogel.

DETAILED DESCRIPTION

Figure 1:
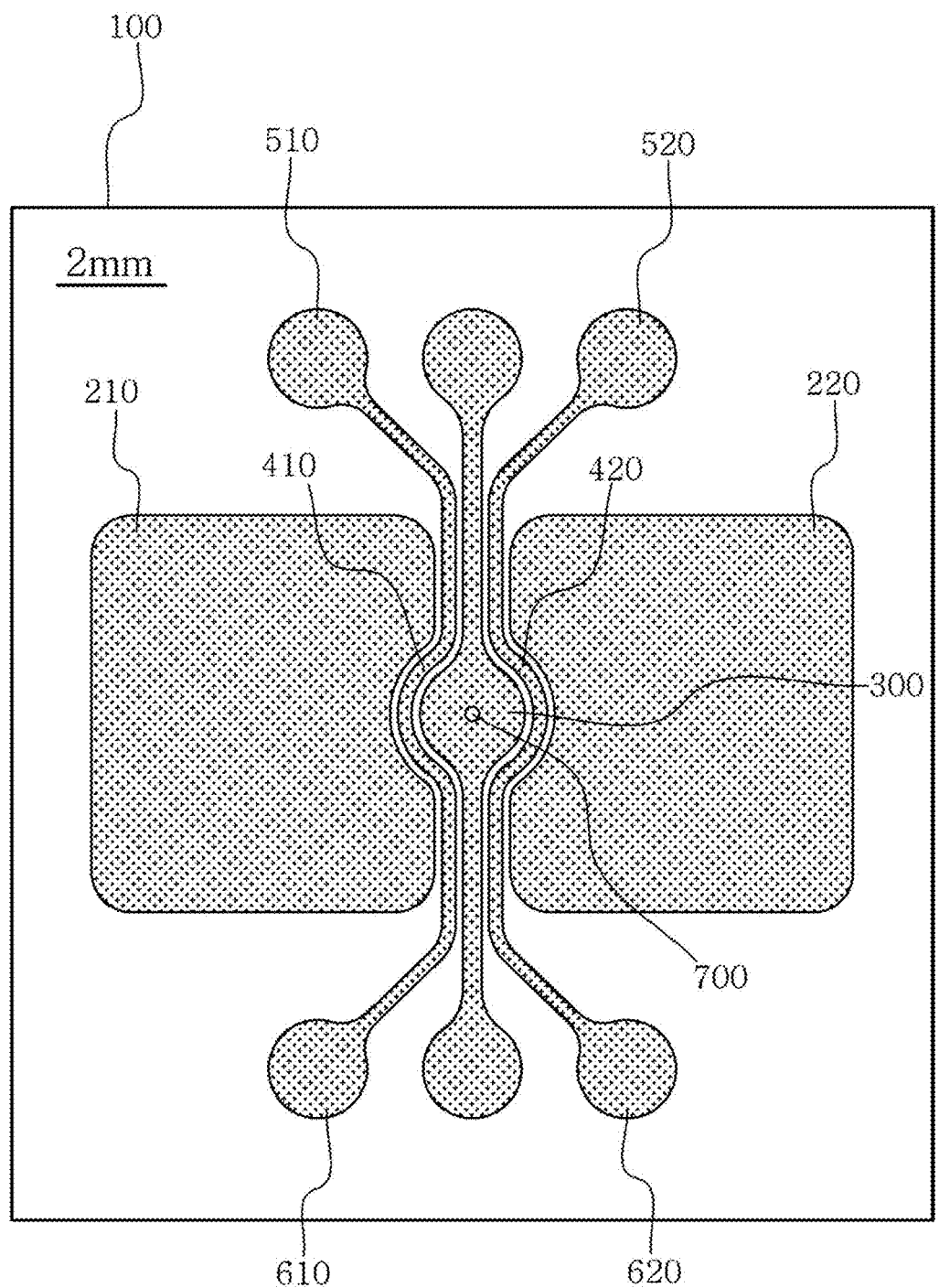
FIG. 1 schematically shows an exemplary microfluidic device 100 designed according to an aspect of the present disclosure.

Hereinafter, a detailed description of the present disclosure is given referring to the attached drawings which illustrate specific exemplary embodiments of the present disclosure. These exemplary embodiments will be described in detail such that those skilled in the art can carry out the present disclosure. It is to be understood that the various exemplary embodiments of the present disclosure need not to be mutually exclusive, although they are different from one another. For example, the particular shape, shape or feature described as an exemplary embodiment may be embodied by another exemplary embodiment without departing from the spirit and scope of the present disclosure. In addition, it is to be understood that the location or arrangement of individual elements in each exemplary embodiment may be changed without departing from the spirit and scope of the present disclosure. Accordingly, the following detailed description is not intended to be limitative and the scope of the present disclosure is limited only by the appended claims and their equivalents.

In an aspect of the present disclosure, a "microenvironment" refers to a small environment which affects the physiological aspects of an individual existing inside the individual. Specifically, it may be a microenvironment present in human, more specifically a microenvironment present in human tissue, further more specifically a tumor microenvironment (TME). However, it is not limited as long as it is a biological microenvironment that can be mimicked with a microfluidic device according to an aspect of the present disclosure.

In an aspect of the present disclosure, a "microfluid" refers to a micro fluid flowing in an individual, more specifically in human tissue. More specifically, it may be a gas or a body fluid flowing through human tumors. Further more specifically, it may be water, blood, lymph, etc. flowing through human tumors or blood vessels around the tumors. The fluid which is not a gas, such as blood, etc., may be replaced in vitro by a fluid including a culture medium or water.

Here, the terms "first" and "second" are only for distinguishing between the type of each element of a microfluidic device of the present disclosure, including diffusion chambers, channels, and the like, and do not limit the order or method of manufacture.

In an aspect, the present disclosure provides a microfluidic device mimicking a biological microenvironment, which includes: a plurality of diffusion chambers; and one or more channel disposed between the plurality of diffusion chambers, wherein the surface of the diffusion chamber and the channel is porous, and wherein the diffusion of a target element between the plurality of diffusion chambers is controlled by interrupting or generating fluid flow inside the channel.

In an aspect of the present disclosure, the diffusion chambers 210, 220, 300 may be chambers wherein a target element loaded in one diffusion chamber is diffused into another adjacent diffusion chamber, and the microfluidic device according to an aspect of the present disclosure mimicking a biological microenvironment may include a plurality of diffusion chambers.

In an aspect of the present disclosure, the shape of the diffusion chamber is not limited as long as it is a 3-dimensional shape in which a biological sample can be loaded. Specifically, the diffusion chamber may have a shape of a plate, a rectangular cuboid, a hemisphere, a sphere, a disc, etc., although not being limited thereto. In an aspect of the present disclosure, the diffusion chamber may be formed of any curable polymer (pre-polymer) material without limitation. The polymer may be a hydrophilic polymer. Specifically, it may be one or more selected from a group consisting of polydimethylsiloxane (PDMS), polystyrene (PS), poly(methyl methacrylate) (PMMA), polytetrafluoroethylene (PTFE), polyethylene (PE), polyurethane (PU), cellulose and silicone rubber, more specifically polydimethylsiloxane, although not being limited thereto.

In an aspect of the present disclosure, the surface of the diffusion chamber may be porous. The diffusion chamber may have a porosity of 10-95 vol % based on the total volume of the diffusion chamber. Specifically, the diffusion chamber may have a porosity of 10 vol % or higher, 15 vol % or higher, 20 vol % or higher, 25 vol % or higher, 30 vol % or higher, 35 vol % or higher, 40 vol % or higher, 45 vol % or higher, 50 vol % or higher, 55 vol % or higher, 60 vol % or higher, 65 vol % or higher, 70 vol % or higher, 75 vol % or higher, 80 vol % or higher, 85 vol % or higher or 90 vol % or higher, and 95 vol % or lower, 90 vol % or lower, 85 vol % or lower, 80 vol % or lower, 75 vol % or lower, 70 vol % or lower, 65 vol % or lower, 60 vol % or lower, 55 vol % or lower, 50 vol % or lower, 45 vol % or lower, 40 vol % or lower, 35 vol % or lower, 30 vol % or lower, 25 vol % or lower, 20 vol % or lower or 15 vol % or lower, more specifically 13.4-27.0 vol %, based on the total volume of the diffusion chamber. However, the porosity may be changed depending on the type of an in-vivo microenvironment to be mimicked with the microfluidic device according to an aspect of the present disclosure, the kind of the target element, the kind of the fluid, the purpose of the mimicking of the microenvironment, etc., although not being limited thereto. In addition, the surface of the diffusion chamber may have a pore size of 5-50 μm. Specifically, the surface of the diffusion chamber may have a pore size of 5 μm or larger, 10 μm or larger, 15 μm or larger, 20 μm or larger, 25 μm or larger, 30 μm or larger, 35 μm or larger, 40 μm or larger or 45 μm or larger, and 50 μm or smaller, 45 μm or smaller, 40 μm or smaller, 35 μm or smaller, 30 μm or smaller, 25 μm or smaller, 20 μm or smaller, 15 μm or smaller or 10 μm or smaller, more specifically 9-42 μm. However, the pore size may be changed depending on the type of an in-vivo microenvironment to be mimicked with the microfluidic device according to an aspect of the present disclosure, the kind of the target element, the kind of the fluid, the purpose of the mimicking of the microenvironment, etc., although not being limited thereto.

In an aspect of the present disclosure, the plurality of diffusion chambers may have the same or different porosity and pore size.

In an aspect of the present disclosure, the channel 410, 420 may be a channel configured such that a fluid can flow therethrough, and the microfluidic device according to an aspect of the present disclosure mimicking a biological microenvironment may include one or more channel. The fluid may be a small-volume fluid flowing in an individual, more specifically in human tissue. More specifically, it may be a gas or a body fluid flowing through human tumors. Further more specifically, it may be water, blood, lymph, etc. flowing through human tumors or blood vessels around the tumors. The fluid which is not a gas, such as blood, etc., may be replaced in vitro by a fluid including a culture medium or water. The kind of the fluid may be changed depending on the type of an in-vivo microenvironment to be mimicked with the microfluidic device according to an aspect of the present disclosure, the kind of the target element, the purpose of the mimicking of the microenvironment, cost, etc.

In an aspect of the present disclosure, a biological sample may be loaded in the plurality of diffusion chambers, and the biological sample contained in each of the plurality of diffusion chambers may have a different concentration of the target element. In an aspect of the present disclosure, the biological sample may be one or more selected from a group consisting of a body fluid isolated from an individual, a culture fluid, a growth factor and a cytokine. Specifically, the culture fluid may be a cell culture fluid. However, the kind of the biological sample may be changed depending on the type of an in-vivo microenvironment to be mimicked with the microfluidic device according to an aspect of the present disclosure, the kind of the target element, the kind of the fluid, the purpose of the mimicking of the microenvironment, etc.

In an aspect of the present disclosure, the channel may be disposed between the diffusion chambers. For example, one channel may be disposed between two diffusion chambers, specifically in the order of chamber-channel-chamber, and they may be arranged in vertical or horizontal directions.

In an aspect of the present disclosure, the channel may have any 3-dimensional shape in which a fluid can flow without limitation. Specifically, the channel may have a cylindrical or prismatic shape, although not being limited thereto. In an aspect of the present disclosure, the channel may be formed of any curable polymer (pre-polymer) material without limitation. The polymer may be a hydrophilic polymer. Specifically, it may be one or more selected from a group consisting of polydimethylsiloxane (PDMS), polystyrene (PS), poly(methyl methacrylate) (PMMA), polytetrafluoroethylene (PTFE), polyethylene (PE), polyurethane (PU), cellulose and silicone rubber, more specifically polydimethylsiloxane, although not being limited thereto.

In an aspect of the present disclosure, the surface of the channel may be porous. The channel may have a porosity of 10-95 vol % based on the total volume of the channel. Specifically, the channel may have a porosity of 10 vol % or higher, 15 vol % or higher, 20 vol % or higher, 25 vol % or higher, 30 vol % or higher, 35 vol % or higher, 40 vol % or higher, 45 vol % or higher, 50 vol % or higher, 55 vol % or higher, 60 vol % or higher, 65 vol % or higher, 70 vol % or higher, 75 vol % or higher, 80 vol % or higher, 85 vol % or higher or 90 vol % or higher, and 95 vol % or lower, 90 vol % or lower, 85 vol % or lower, 80 vol % or lower, 75 vol % or lower, 70 vol % or lower, 65 vol % or lower, 60 vol % or lower, 55 vol % or lower, 50 vol % or lower, 45 vol % or lower, 40 vol % or lower, 35 vol % or lower, 30 vol % or lower, 25 vol % or lower, 20 vol % or lower or 15 vol % or lower, more specifically 13.4-27.0 vol %, based on the total volume of the channel. However, the porosity may be changed depending on the type of an in-vivo microenvironment to be mimicked with the microfluidic device according to an aspect of the present disclosure, the kind of the target element, the kind of the fluid, the purpose of the mimicking of the microenvironment, etc., although not being limited thereto. In addition, the surface of the channel may have a pore size of 5-50 μm. Specifically, the surface of the channel may have a pore size of 5 μm or larger, 10 μm or larger, 15 μm or larger, 20 μm or larger, 25 μm or larger, 30 μm or larger, 35 μm or larger, 40 μm or larger or 45 μm or larger, and 50 μm or smaller, 45 μm or smaller, 40 μm or smaller, 35 μm or smaller, 30 μm or smaller, 25 μm or smaller, 20 μm or smaller, 15 μm or smaller or 10 μm or smaller, more specifically 9-42 μm. However, the pore size may be changed depending on the type of an in-vivo microenvironment to be mimicked with the microfluidic device according to an aspect of the present disclosure, the kind of the target element, the kind of the fluid, the purpose of the mimicking of the microenvironment, etc., although not being limited thereto.

In an aspect of the present disclosure, the porosity and pore size of the one or more channels may be the same or different.

In an aspect of the present disclosure, the microfluidic device can control the diffusion of a target element between the plurality of diffusion chambers by interrupting or generating fluid flow inside the channel.

In an aspect of the present disclosure, the target element may be a target element loaded inside the diffusion chamber or a target element included in a biological sample loaded inside the diffusion chamber. The target element may be a cell or a molecule present in a biological microenvironment to be mimicked with the microfluidic device according to an aspect of the present disclosure, which may be a cell or a molecule affecting the change in an in-vivo microenvironment, and may be a control target of the microfluidic device according to an aspect of the present disclosure. The target element may be specifically a cell or a molecule, more specifically one or more selected from a group consisting of a cell, a growth factor, a chemokine, a cytokine, a hypoxia-inducible factor and an antibody. Further more specifically, the cell may be one or more selected from a group consisting of a cancer cell, an immune cell, a fibroblast, an endothelial cell and an epithelial cell. However, the target element may be different depending on the type of an in-vivo microenvironment to be mimicked with the microfluidic device according to an aspect of the present disclosure, the purpose of the mimicking of the microenvironment, etc., although not being limited thereto.

In an aspect of the present disclosure, the diffusion control of the target element may be achieved as the diffusion of the target element between the plurality of diffusion chambers is interrupted when fluid flow is generated inside the channel and the diffusion of the target element occurs between the plurality of diffusion chambers when the fluid flow is interrupted inside the channel. In addition, the diffusion of the target element may be achieved through pores on the surface of the diffusion chambers and the channel. Specifically, when fluid flow is generated inside a channel of the microfluidic device according to an aspect of the present disclosure mimicking a biological microenvironment, the diffusion between the diffusion chambers adjacent to the channel with the fluid flow generated may be interrupted. And, when fluid flow is generated inside a channel of the microfluidic device according to an aspect of the present disclosure mimicking a biological microenvironment, the target element may be transported through diffusion from a diffusion chamber where the target element is present at a higher concentration to a diffusion chamber where the target element is present at a lower concentration, among diffusion chambers adjacent to the channel with the fluid flow generated. More specifically, when fluid flow is generated in a first channel disposed between a first diffusion chamber and a second diffusion chamber, the interaction between the first diffusion chamber and the second diffusion chamber may be interrupted and, furthermore, the diffusion between the first diffusion chamber and the second diffusion chamber may be interrupted with no movement of the target element present in the first diffusion chamber or the second diffusion chamber. In addition, more specifically, when fluid flow is interrupted in the first channel disposed between the first diffusion chamber and the second diffusion chamber, interaction may occur between the first diffusion chamber and the second diffusion chamber and, furthermore, if the target element is present in the first diffusion chamber at a higher concentration and the target element is present in the second diffusion chamber at a lower concentration, the target element may be moved or diffused to the second diffusion chamber through the first channel, specifically through the pores on the surface of the first channel.

In an aspect of the present disclosure, the surface of the plurality of diffusion chambers 210, 220, 300 and the one or more channel 410, 420 may include a porous wall 811, 812, 821, 822.

In an aspect of the present disclosure, the microfluidic device mimicking a biological microenvironment may further include a diffusion control unit, and the diffusion control unit may include: one or more inlet 510, 520 through which a fluid is introduced into the one or more channel, respectively; and one or more outlet 610, 620 through which the introduced fluid is discharged. The inlet and the outlet may be present on either end of one channel, respectively.

In an aspect of the present disclosure, the microfluidic device mimicking a biological microenvironment may include a porous substrate. The microfluidic device mimicking a biological microenvironment may have the plurality of diffusion chambers and the one or more channel on the porous substrate. The porous substrate may have a porosity of 10-95 vol % based on the total volume of the substrate. Specifically, the porous substrate may have a porosity of 10 vol % or higher, 15 vol % or higher, 20 vol % or higher, 25 vol % or higher, 30 vol % or higher, 35 vol % or higher, 40 vol % or higher, 45 vol % or higher, 50 vol % or higher, 55 vol % or higher, 60 vol % or higher, 65 vol % or higher, 70 vol % or higher, 75 vol % or higher, 80 vol % or higher, 85 vol % or higher or 90 vol % or higher, and 95 vol % or lower, 90 vol % or lower, 85 vol % or lower, 80 vol % or lower, 75 vol % or lower, 70 vol % or lower, 65 vol % or lower, 60 vol % or lower, 55 vol % or lower, 50 vol % or lower, 45 vol % or lower, 40 vol % or lower, 35 vol % or lower, 30 vol % or lower, 25 vol % or lower, 20 vol % or lower or 15 vol % or lower, more specifically 13.4-27.0 vol %, based on the total volume of the substrate. However, the porosity may be changed depending on the type of an in-vivo microenvironment to be mimicked with the microfluidic device according to an aspect of the present disclosure, the kind of the target element, the kind of the fluid, the purpose of the mimicking of the microenvironment, etc., although not being limited thereto. In addition, the surface of the porous substrate may have a pore size of 5-50 μm. Specifically, the surface of the porous substrate may have a pore size of 5 μm or larger, 10 μm or larger, 15 μm or larger, 20 μm or larger, 25 μm or larger, 30 μm or larger, 35 μm or larger, 40 μm or larger or 45 μm or larger, and 50 μm or smaller, 45 μm or smaller, 40 μm or smaller, 35 μm or smaller, 30 μm or smaller, 25 μm or smaller, 20 μm or smaller, 15 μm or smaller or 10 μm or smaller, more specifically 9-42 μm. However, the pore size may be changed depending on the type of an in-vivo microenvironment to be mimicked with the microfluidic device according to an aspect of the present disclosure, the kind of the target element, the kind of the fluid, the purpose of the mimicking of the microenvironment, etc., although not being limited thereto. The porosity or pore size of the porous substrate may be identical to or different from the porosity or pore size of the plurality of diffusion chambers or the porosity or pore size of the one or more channel.

In an aspect of the present disclosure, one or more of the plurality of diffusion chambers may include a supporting member 700 therein. In an aspect of the present disclosure, when the diffusion chamber includes a supporting member therein, bubbles generated in a part of the chamber may be removed and, through this, the movement or diffusion of the target material included in the biological sample loaded in the diffusion chamber may be facilitated.

In another aspect, the present disclosure provides a method for manufacturing a microfluidic device mimicking a biological microenvironment, which includes: preparing a device-forming solution including a pre-polymer; forming a substrate by coating a scaffold solution including a polymer on a plate and forming a cavity in the substrate; and forming a microfluidic device by injecting the device-forming solution into the cavity formed in the substrate and curing the same. The microfluidic device mimicking a biological microenvironment, the channel, etc. are the same as described above.

The method for manufacturing a microfluidic device according to an aspect of the present disclosure may include preparing a device-forming solution including a pre-polymer.

In an aspect of the present disclosure, the "pre-polymer" refers to a preliminary polymer whose polymerization or polycondensation has been stopped at an appropriate stage for easy molding of a polymer. In an aspect of the present disclosure, it may be a polymer in an easily moldable state before it is cured, and may be a hydrophilic polymer. The pre-polymer solution may include a pore-inducing polymer (porogen), and the manufacturing method may further include controlling the size of pores formed in a porous structure by changing the size of the pore-inducing polymer included in the pre-polymer solution. The pore-inducing polymer may be polyethylene glycol (PEG), polyacrylamide (PAM), etc., and the polyethylene glycol may be specifically PEG200, PEG300, PEG400, PEG600, PEG1000, PEG1500, PEG2000, PEG3000, PEG3350, PEG4000, PEG6000, PEG8000, PEG10000, PEG12000, PEG20000, PEG35000, PEG40000, etc. (manufactured by Sigma Aldrich).

The method for preparing a microfluidic device according to an aspect of the present disclosure may include forming a substrate by coating a scaffold solution including a polymer on a plate and forming a cavity in the substrate.

In an aspect of the present disclosure, the scaffold solution may be any solution including a curable polymer (pre-polymer) without limitation. The polymer may be a hydrophilic polymer. Specifically, it may be one or more selected from a group consisting of polydimethylsiloxane (PDMS), polystyrene (PS), poly(methyl methacrylate) (PMMA), polytetrafluoroethylene (PTFE), polyethylene (PE), polyurethane (PU), cellulose and silicone rubber, more specifically polydimethylsiloxane, although not being limited thereto.

In an aspect of the present disclosure, the plate may be specifically a glass slide, although not being limited thereto.

In an aspect of the present disclosure, the forming a substrate may be coating a mixture of the scaffold solution and a curing agent on a plate and then heating the same. The mixing ratio of the scaffold solution and the curing agent, the method and condition of the coating and the temperature and time of the heating may be changed depending on the type of an in-vivo microenvironment to be mimicked with the microfluidic device, the kind of the target element, the purpose of the mimicking of the microenvironment, etc.

In an aspect of the present disclosure, the formation of the cavity in the substrate may be achieved by cutting a part of the formed substrate to form a cavity, i.e., a void space, in the substrate.

The method for manufacturing a microfluidic device according to an aspect of the present disclosure may include forming a microfluidic device by injecting the device-forming solution into the cavity formed in the substrate and curing the same. In an aspect of the present disclosure, the forming a microfluidic device may specifically include injecting the device-forming solution into the cavity formed in the substrate, curing the same and etching a plurality of diffusion chambers and one or more channel to form the microfluidic device. More specifically, it may include injecting the device-forming solution into the cavity formed in the substrate, curing the same, etching a plurality of diffusion chambers and one or more channel and then covering and engaging a polymer layer to form the microfluidic device.

In an aspect of the present disclosure, the etching pattern may be determined in consideration of the number and shape of the diffusion chambers of the microfluidic device desired to be manufactured without limitation. And, the curing may be performed specifically by an optical, chemical or thermal curing method, without limitation. For example, UV curing may be employed. In addition, the manufacturing method may further include washing after the curing. Through the washing, the pore-inducing polymer, etc. which have not been reacted may be removed.

In another aspect, the present disclosure provides a method for controlling a microenvironment in real time, which includes: interrupting or generating fluid flow inside one or more channel among the one or more channel of the microfluidic device mimicking a biological microenvironment described above. The microfluidic device mimicking a biological microenvironment, the channel, the interruption or generation of fluid flow, etc. are the same as described above.

In an aspect of the present disclosure, the interruption of fluid flow may be achieved by discharging all the fluid present inside the channel so that no fluid is present inside the channel, and the generation of fluid flow may be achieved by injecting a fluid into the channel so that the fluid is present inside the channel. In addition, the diffusion of the target element between the plurality of diffusion chambers may be controlled with the interruption or generation of fluid flow.

In another aspect, the present disclosure provides a method for measuring and observing cellular response using a microfluidic device, which includes: loading a biological sample in one or more diffusion chamber among the one or more diffusion chamber of the plurality of diffusion chambers of the microfluidic device mimicking a biological microenvironment described above; and interrupting or generating fluid flow inside one or more channel among the one or more channel. The microfluidic device mimicking a biological microenvironment, the diffusion chamber, the biological sample, the channel, the interruption or generation of fluid flow, etc. are the same as described above.

In an aspect of the present disclosure, the cellular response may include, for example, the migration of a cell, the change in cell morphology, the change in the migration speed of a cell, the change in the proliferation of a cell, the change in division pattern of a cell, the infiltration of a cell to another tissue, the necrosis of a cell, etc., and the cell may include a bacterial, etc., although not being limited thereto.

Hereinafter, the constitution and effect of the present disclosure are described more specifically referring to examples and test examples. However, the following examples and test examples are provided only for the purpose of easier understanding of the present disclosure, and the category and scope of the present disclosure are not limited by them.

[Example 1] Design of Microfluidic Device

Figure 2A:
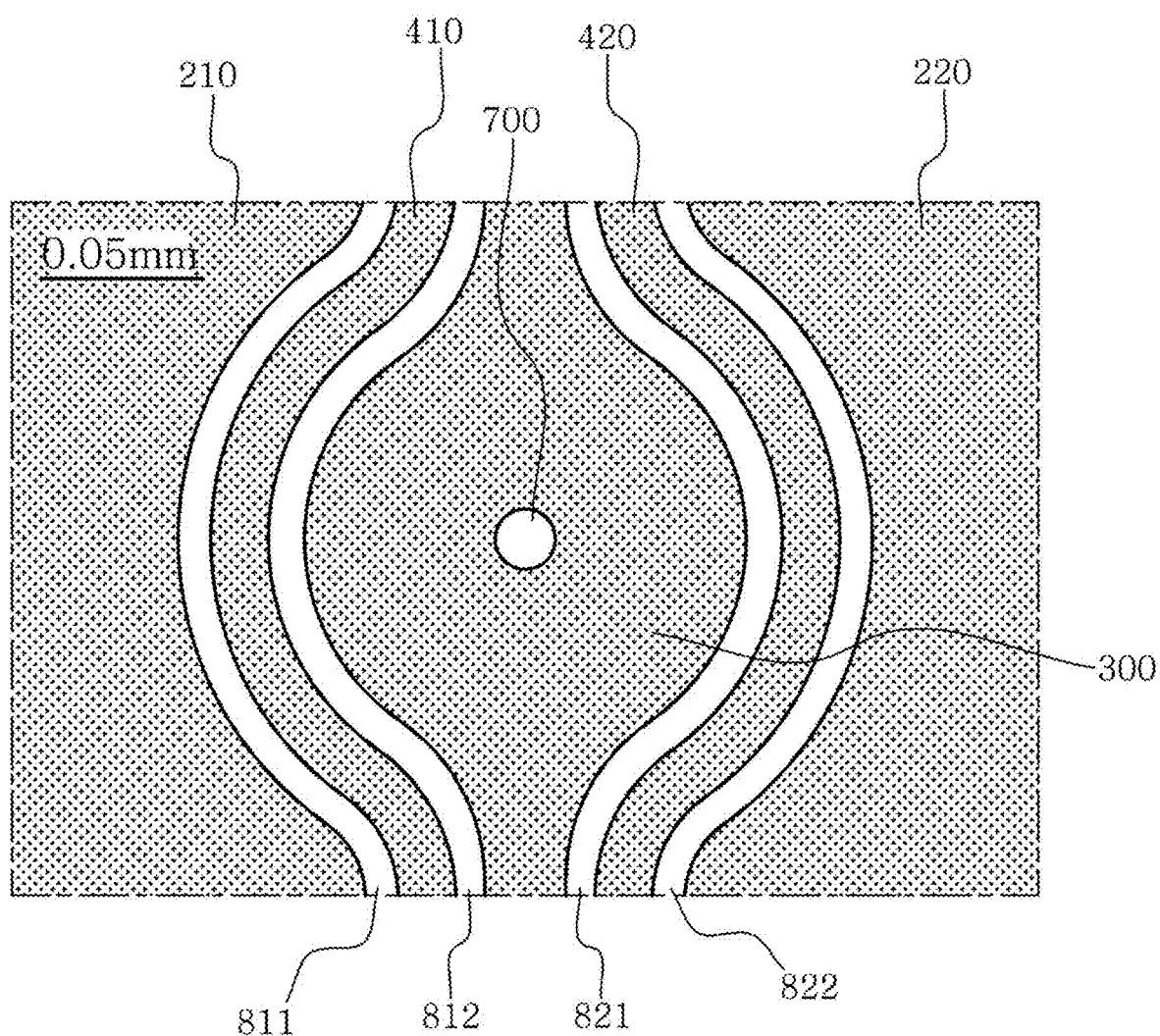
FIGS. 2A and 2B magnify the central diffusion chamber portion of FIG. 1 and show an exemplary microfluidic device 100 designed according to an aspect of the present disclosure.
Figure 2B:
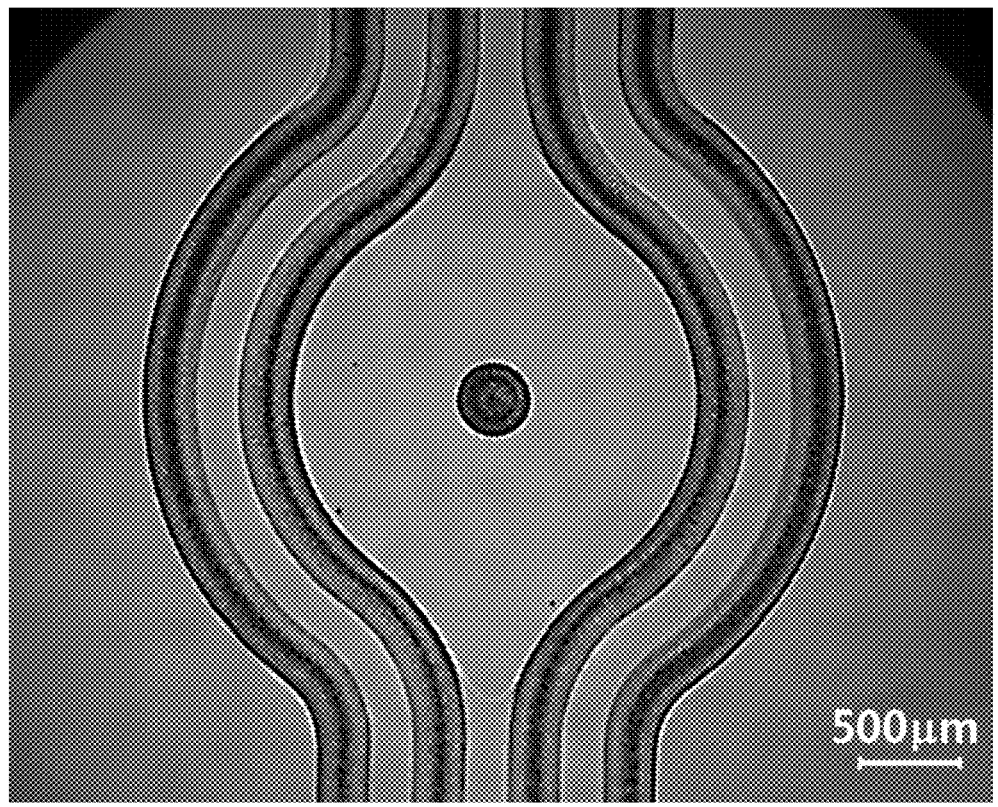

A microfluidic device was designed in order to manufacture a microfluidic device mimicking a biological microenvironment according to an aspect of the present disclosure. FIG. 1 and FIGS. 2A and 2B schematically show an exemplary microfluidic device designed according to an aspect of the present disclosure.

Specifically, in FIG. 1, FIGS. 2A and 2B, the portions represented by black lines and white parts represent a porous hydrogel, and the portions represented by dots represent channels and diffusion chambers. A microfluidic device 100 of FIG. 1 has a first side diffusion chamber 210, a second side diffusion chamber 220 and one central diffusion chamber 300 as diffusion chambers. They serve for cell proliferation or as a supply source of growth factors. A channel is disposed between the side chambers and the central chamber for diffusion control by a hydrogel. Specifically, a first channel 410 is disposed between the first side diffusion chamber 210 and the central diffusion chamber 300, and a second channel 420 is disposed between the central diffusion chamber 300 and the second side diffusion chamber 220. If a fluid is introduced into the channel, a chemical substance that has been diffused into the channel and has been present inside the channel is removed from the channel due to fluid flow, and the diffusion of a chemical substance between the diffusion chambers is interrupted. And, if fluid flow in the channel is interrupted, diffusion of a chemical substance occurs between the diffusion chambers. A microfluidic device including a channel (diffusion switch channel) which operates as a switch turning on/off the diffusion of a target element (chemical substance) between diffusion chambers was tested by COMSOL simulation, and the result is shown in FIG. 3.

Figure 3:
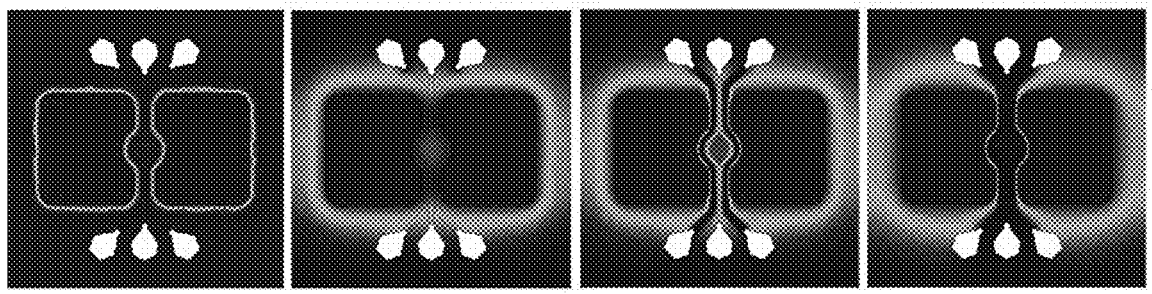
FIG. 3 shows a COMSOL simulation result of a microfluidic device 100 designed according to an aspect of the present disclosure. Specifically.

As shown in FIG. 3, if the diffusion switch is turned on by interrupting fluid flow in the channel, the diffusion of a target element occurs between the diffusion chambers. And, if the diffusion switch is turned off by generating fluid flow in the channel, the interaction between the diffusion chambers is interrupted and the target element that has been diffused into the channel from the diffusion chambers is removed, and the device is returned to its pervious state until the diffusion switch is turned on again. Through this, the diffusion of the target element between the diffusion chambers can be controlled via a simple method of interrupting or generating fluid flow in the channel.

However, bubbles can be formed easily by the fluid flow because of layer separation at the boundary due to the convex shape of the central diffusion chamber 300. The bubbles make it difficult to embody a stable biological microenvironment because they move constantly inside the diffusion chambers when the fluid flow is formed. In addition, the bubbles formed by the fluid flow may have a small size due to fluid pressure, but when the fluid flow is interrupted the size of the bubbles may be increased since the fluid pressure is decreased. If the inside of the diffusion chambers is filled with bubbles through this process, it is difficult to mimic the biological microenvironment since the target element is not diffused uniformly into the adjacent diffusion chambers. Accordingly, when manufacturing the microfluidic device according to an aspect of the present disclosure, the inventors of the present disclosure have disposed a supporting member 700 as a support column inside the central diffusion chamber 300 to prevent bubble formation during fluid inflow.

[Example 2] Manufacturing of Microfluidic Device

Figure 4:
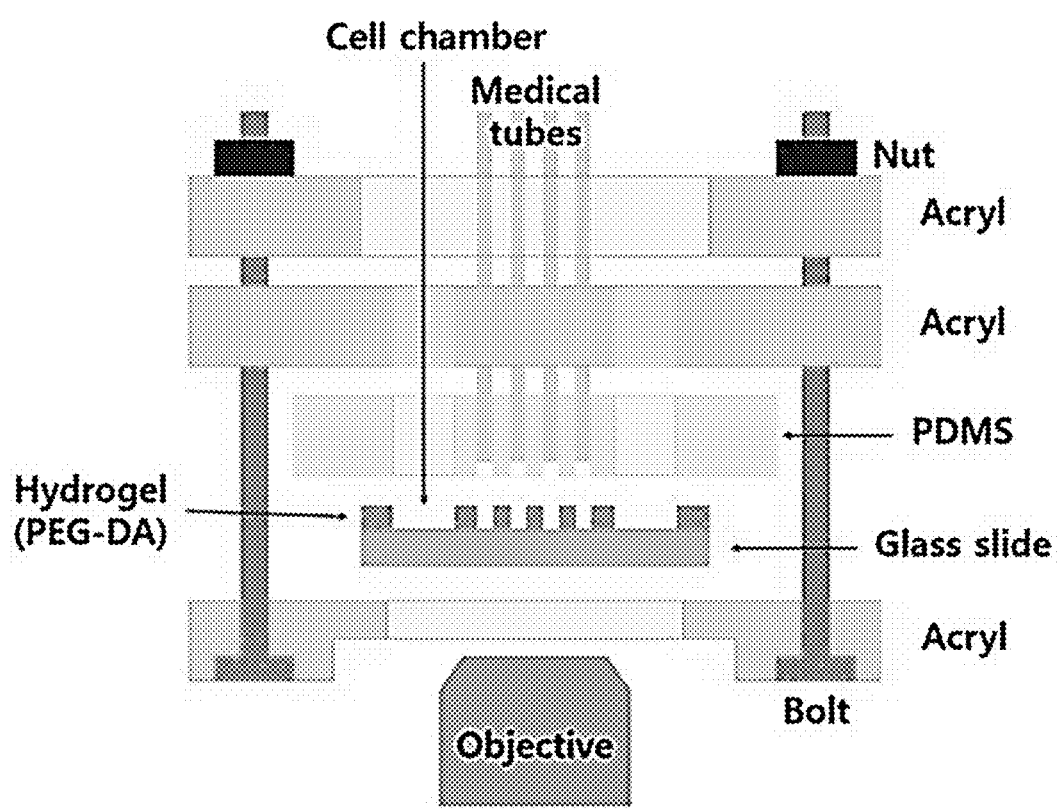
FIG. 4 schematically shows the configuration of a microfluidic device according to an aspect of the present disclosure and a process of manufacturing the same.
Figure 5:
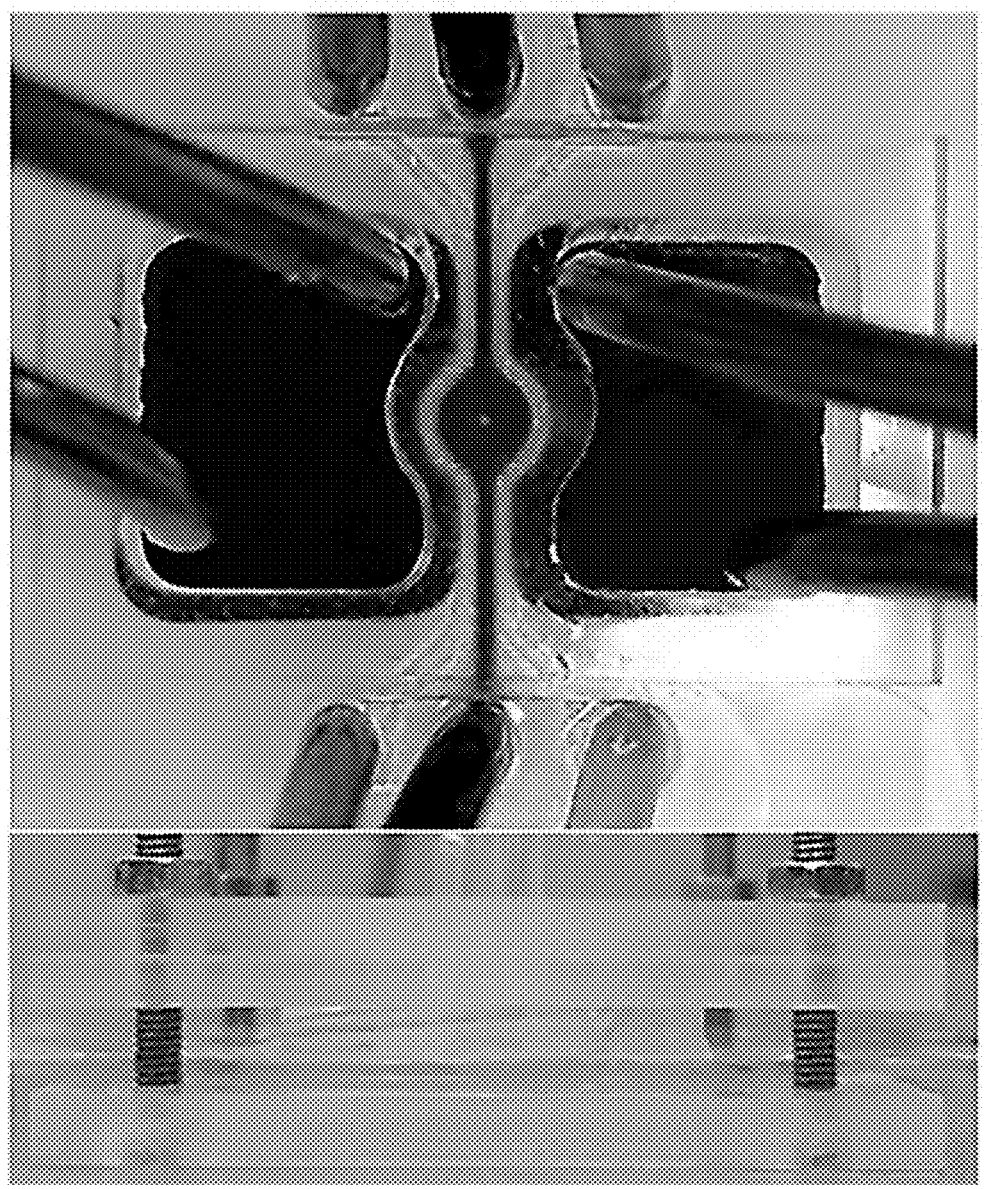
FIG. 5 is a photograph of a microfluidic device manufactured according to an aspect of the present disclosure.
Figure 6:
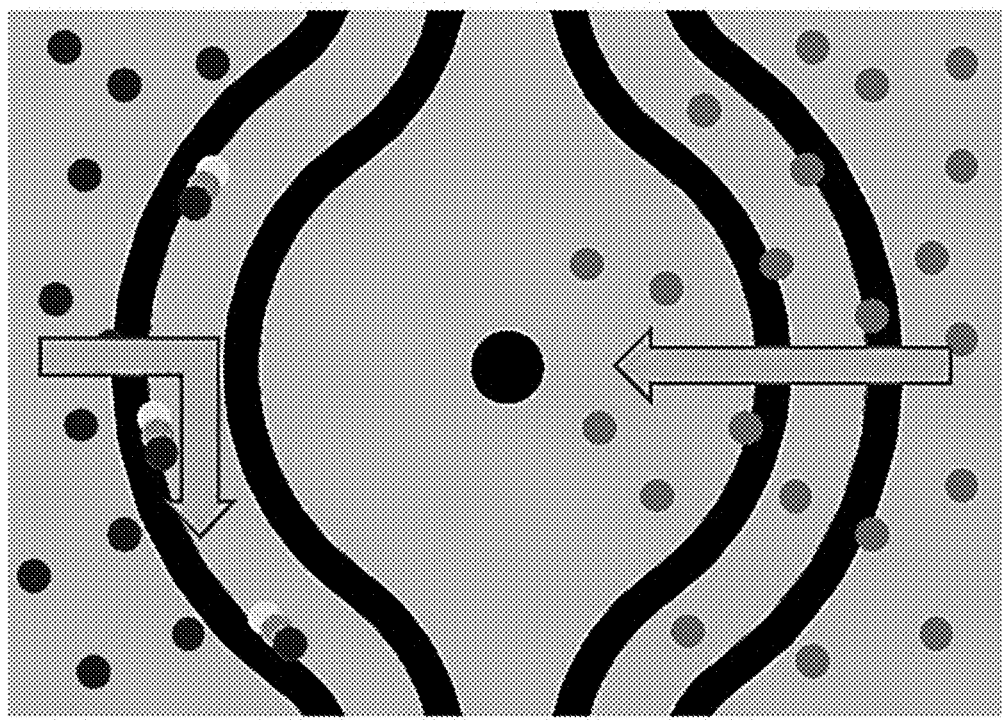
FIG. 6 schematically shows a diffusion switching mechanism whereby the diffusion of a target element between diffusion chambers is controlled by interrupting (no flow) or generating (flow) fluid flow inside a channel using a microfluidic device according to an aspect of the present disclosure.

A microfluidic device according to an aspect of the present disclosure was manufactured based on the microfluidic device design and simulation test result of Example 1. FIGS. 4 and 5 show the configuration and manufacturing process of the microfluidic device according to an aspect of the present disclosure.

Specifically, the microfluidic device according to an aspect of the present disclosure was manufactured as a porous microfluidic device using a polyethylene glycol diacrylate solution (PEG-DA, Sigma-Aldrich, MW=700 Da, 10% (v/v) in PBS) mixed with photoinitiator Irgacure 2959 (Sigma-Aldrich, St. Louis, MO) at a concentration of 0.5% (w/v), as a pre-polymer solution. In order to form a PEG-DA channel on a glass slide, a polydimethylsiloxane (PDMS, SYLGARD 184, Dow Corning, USA) scaffold with a height of 200 μm was polymerized in advance on a glass slide. Specifically, the polymerization was performed as follows. After mixing PDMS with a curing agent (SYLGARD 184 silicone elastomer curing agent, Dow Corning) at a ratio of 10:1 (w/w) and spin-coating on a glass slide for 15 seconds at 500 rpm, a PDMS layer with a height of 200 μm was prepared by heating on a hot plate at 90° C. for 30 minutes. Then, a square shape of 23 mm×23 mm was cut in the center of the coated glass slide to peel off the PDMS layer to form a square-shaped space at the center of the formed PDMS scaffold. Then, after pouring the prepared pre-polymer solution into the empty central space of the PDMS layer, diffusion chamber and channel patterns were etched on the hydrogel (PEG-DA) substrate for 57.5 seconds using a photomask (Microtech, 40000 dpi, Korea) and a UV curing system (365 nm, 18 W/cm$^2$, Omnicure S1500, Vanier, Quebec). After covering the glass slide with the PDMS layer, the microfluidic device according to an aspect of the present disclosure was manufactured by assembling with acryl plates using bolts and nuts.

[Test Example 1] Confirmation of Diffusion Switching Mechanism

In order to confirm a diffusion switching mechanism whereby the diffusion of a target element occurs between the diffusion chambers of the microfluidic device manufactured in Example 2 depending on the interruption or generation of fluid flow inside the channel, a diffusion control experiment was conducted by loading two different fluorescent dyes in the diffusion chambers, respectively.

Figure 7:
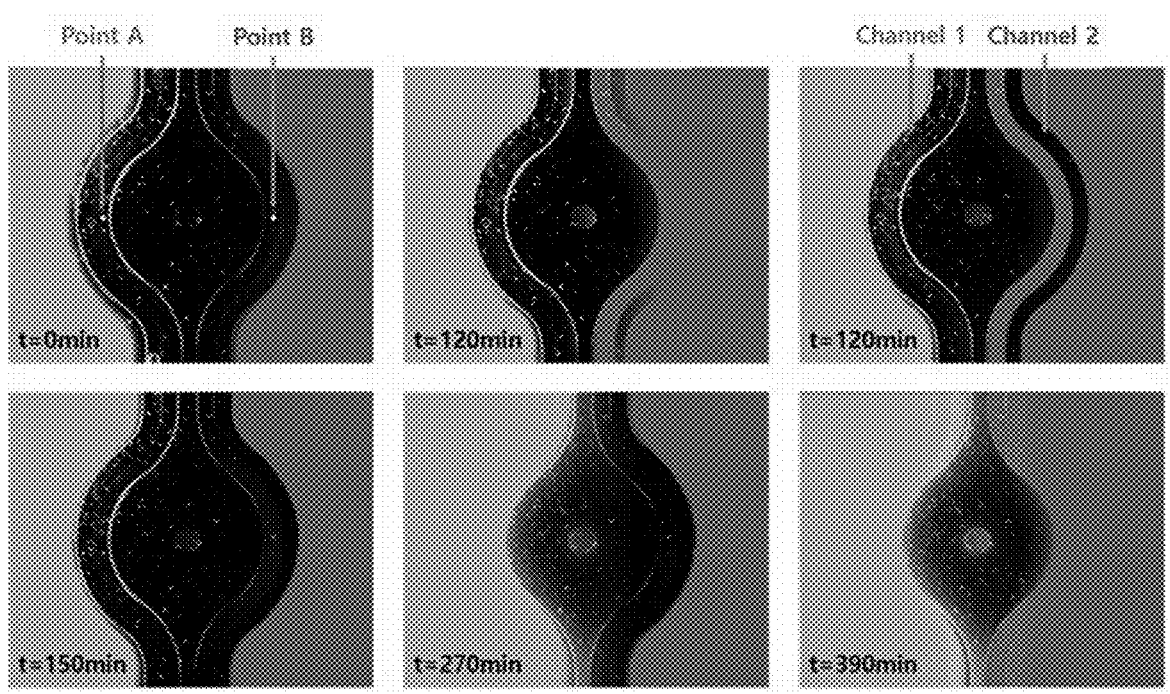
FIG. 7 shows fluorescence images obtained with time in a diffusion control experiment conducted to investigate a diffusion switching mechanism whereby the diffusion of a target element occurs between diffusion chambers in a microfluidic device according to an aspect of the present disclosure depending on interruption or generation of fluid flow inside a channel.
Figure 8:
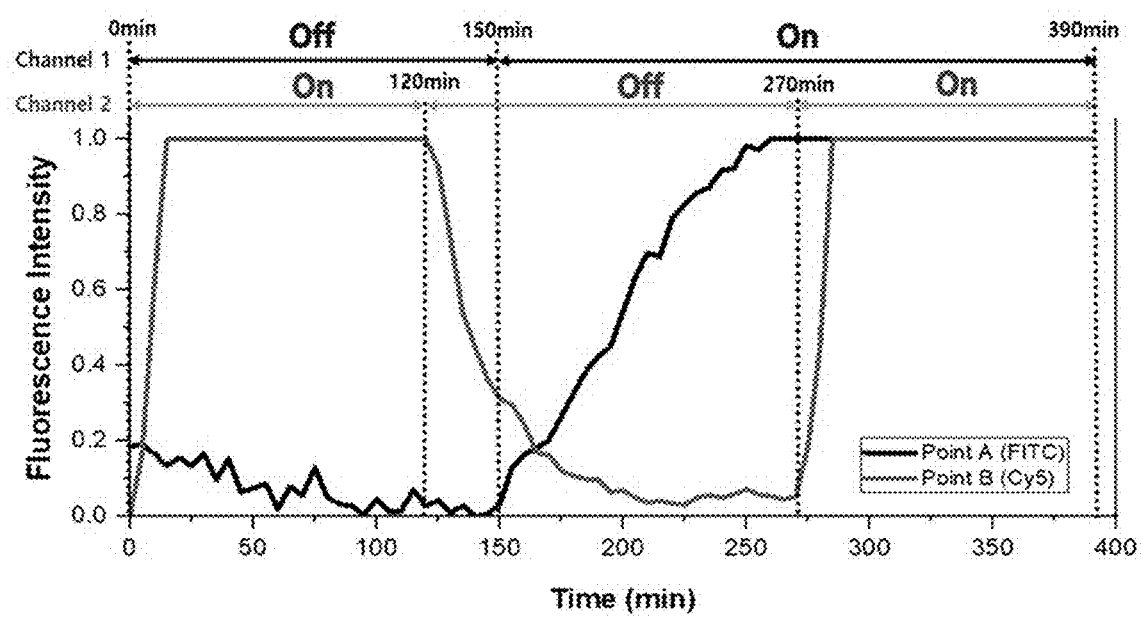
FIG. 8 shows the fluorescence intensity at point A and point B in FIG. 7 with time.

Specifically, a solution of fluorescein 5(6)-isothiocyanate (FITC, Sigma-Aldrich, 0.1 mg/mL) emitting green color and a solution of cyanine 5 (Cy5, Thermo Fisher Scientific, 0.01 mg/mL) emitting red color were loaded into the first side diffusion chamber 210 and the second side diffusion chamber 220 of the microfluidic device, respectively. Then, the diffusion of the two fluorescent dyes was observed for 6.5 hours using a fluorescence microscope (Zeiss Axio Observer) and the result was quantified using the obtained microscopic images. The result is shown in FIGS. 7 and 8. FIGS. 7 and 8 show the result of analyzing the retention time of the diffused fluorescent dyes (light gray: FITC, dark gray: Cy5) in the side chambers and the central chamber and the change in their concentration. Specifically, FIG. 7 shows the fluorescence images obtained at different times, and FIG. 8 shows the fluorescence intensity at A and point B of FIG. 7, respectively. Fluid flow inside the channel was generated or interrupted at specific concentrations.

As shown in FIGS. 7 and 8, the fluorescent dyes loaded in the diffusion chambers were diffused or moved to the other diffusion chambers through the channel when fluid flow was interrupted in the channel. In contrast, when fluid flow was generated in the channel, the diffusion or movement of the fluorescent dyes was interrupted. Specifically, when the diffusion switch of Cy5 (red) was turned on as fluid flow in the second channel (channel 2) 420 was interrupted at 0 minute, the fluorescence intensity of Cy5 in the second side diffusion chamber 220 in which Cy5 is loaded was increased until maximum and the fluorescence intensity was maintained until the diffusion switch of Cy5 was turned off as fluid flow was generated in the second channel 420 at 120 minutes. When the diffusion switch was turned off as fluid flow was generated in the second channel 420, the fluorescence intensity of the Cy5-loaded second side diffusion chamber 220 in which Cy5 is loaded was decreased to the initial value. In addition, when the diffusion switch of FITC (green) was turned on as fluid flow in the first channel (channel 1) 410 interrupted at 150 minutes, the same diffusion pattern was observed as the Cy5. Although FITC was diffused at a slower rate than Cy5 due to the difference in the diffusion-related parameters of the target elements, Cy5 and FITC, the diffusion pattern, i.e., the diffusion pattern of the target element between the diffusion chambers depending on the interruption or generation of fluid flow in the channel, was the same as that of Cy5. In addition, as already confirmed in the COMSOL simulation of Example 1 (FIG. 3), the channel absorbed the target element molecules diffused to the central diffusion chamber from among the diffusion chambers while fluid flow was generated in the channel (diffusion switch off) (the target element was diffused from the central diffusion chamber to the channel) and the device was returned to the initial state.

Through this, it was confirmed that, because the microfluidic device according to an aspect of the present disclosure is capable of controlling the microenvironment with time through control of the diffusion of a target element between the diffusion chambers via a simple method of interrupting or generating fluid flow inside the channel, the microfluidic device can mimic the biological microenvironment constantly changing with time.

[Test Example 2] Confirmation of Diffusion of Growth Factor Using Diffusion Switching Mechanism and Control of Cell Proliferation with Time Thereby It was confirmed whether an in-vivo microenvironment can be controlled with time by culturing cells in the microfluidic device manufactured in Example 2.

Cells involved in angiogenesis, growth factors, etc. were used to realize a tumor microenvironment (TME) as one of in-vivo microenvironments. In the tumor microenvironment, angiogenic response is controlled, i.e., switched on/off, by the coexistence of tumors, macrophages and fibroblasts, and angiogenesis is characterized by increased cellular proliferation and transport of growth factors (D. Ribatti, B. Nico, E. Crivellato, A. M. Roccaro, and A. Vacca, "The history of the angiogenic switch concept," *Leukemia*, vol. 21, no. 1, pp. 44-52, 2007).

For this, the following three types of cells were cultured in the media described below, under the condition of 37° C. and 5% $CO_2$:

Human hepatocellular carcinoma cells (HepG2, Korean Cell Line Bank KCLB No. 88065) were cultured in Eagle's minimum essential medium (EMEM, Welgene) containing 10% (v/v) fetal bovine serum (FBS, Gibco).

Mouse macrophage cells (RAW 264.7, Korean Cell Line Bank KCLB No. 40071) were cultured in Dulbecco's modified Eagle's medium (DMEM, Gibco) containing 10% (v/v) FBS.

Human umbilical vein endothelial cells (HUVEC, ATCC CRL-1730) were cultured in endothelial cell medium (ECM, ScienCell) containing 5% (v/v) FBS, 1% (v/v) endothelial cell growth supplement (ECGS) and 1% (v/v) antibiotic solution.

Figure 9:
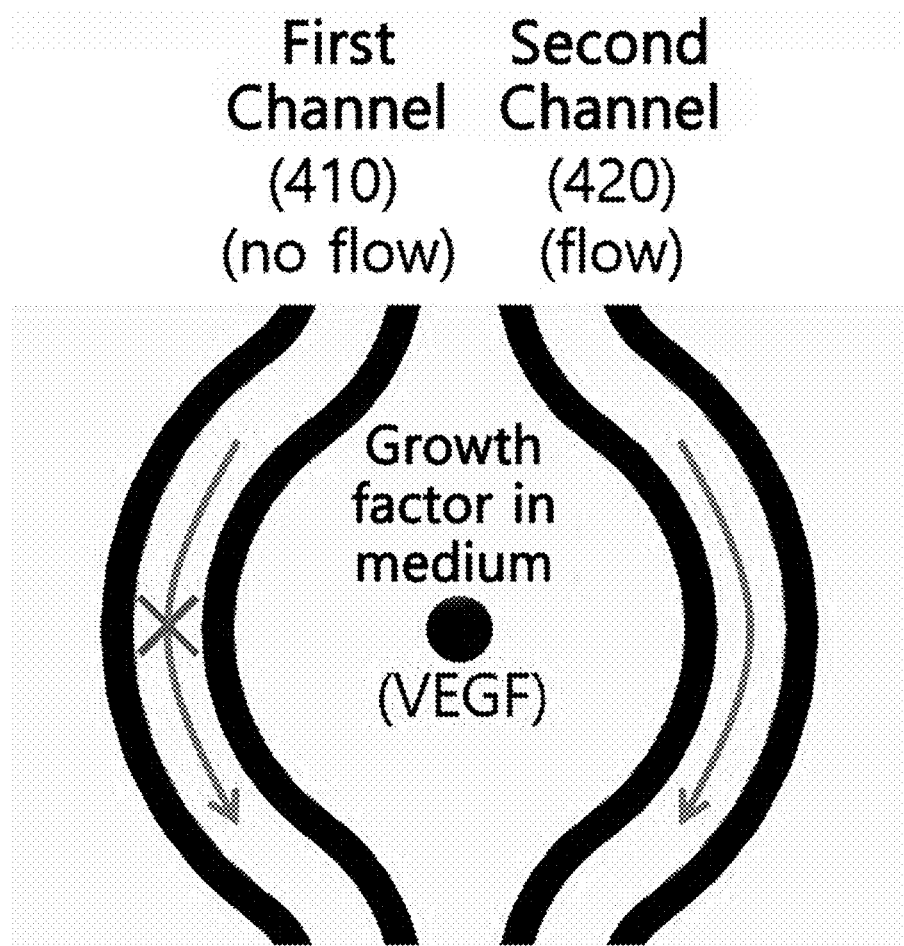
FIG. 9 schematically shows a diffusion switching mechanism whereby the diffusion of a growth factor (VEGF) existing in a central diffusion chamber is controlled by interrupting or generating fluid flow inside the channel using a microfluidic device according to an aspect of the present disclosure.

Then, after coating the first and second side diffusion chambers 210, 220 of the microfluidic device of Example 2 with fibronectin (Corning 356008) at a concentration of 5 μg/cm$^2$ for 45 minutes, the cultured endothelial cells (HUVEC) were added therein and kept at 37° C. and 5% $CO_2$. Also, in order to mimic tumor and tumor-associated cellular environments, culture fluids of the human hepatocellular carcinoma cells (HepG2) and the mouse macrophage cells (RAW 264.7) cultured for 48 hours were mixed with 20 ng/mL VEGF at a ratio of 1:1. Then, after adding the mixed culture fluid to the central diffusion chamber 300 of the microfluidic device of Example 2 as a medium for turning the angiogenic switch on, fluid flow was generated (diffusion switch off) in only one channel (second channel 420) among the channels disposed on both sides of the central diffusion chamber 300 by injecting the fluid and fluid flow in the other channel (first channel 410) was interrupted (diffusion switch on) as schematically shown in FIG. 9. In this state, the proliferation of the endothelial cells (HUVEC) loaded in the first and second side diffusion chambers 210, 220 was measured. The endothelial cells (HUVEC) loaded in the side diffusion chambers were cultured in ECM medium.

Figure 10A:
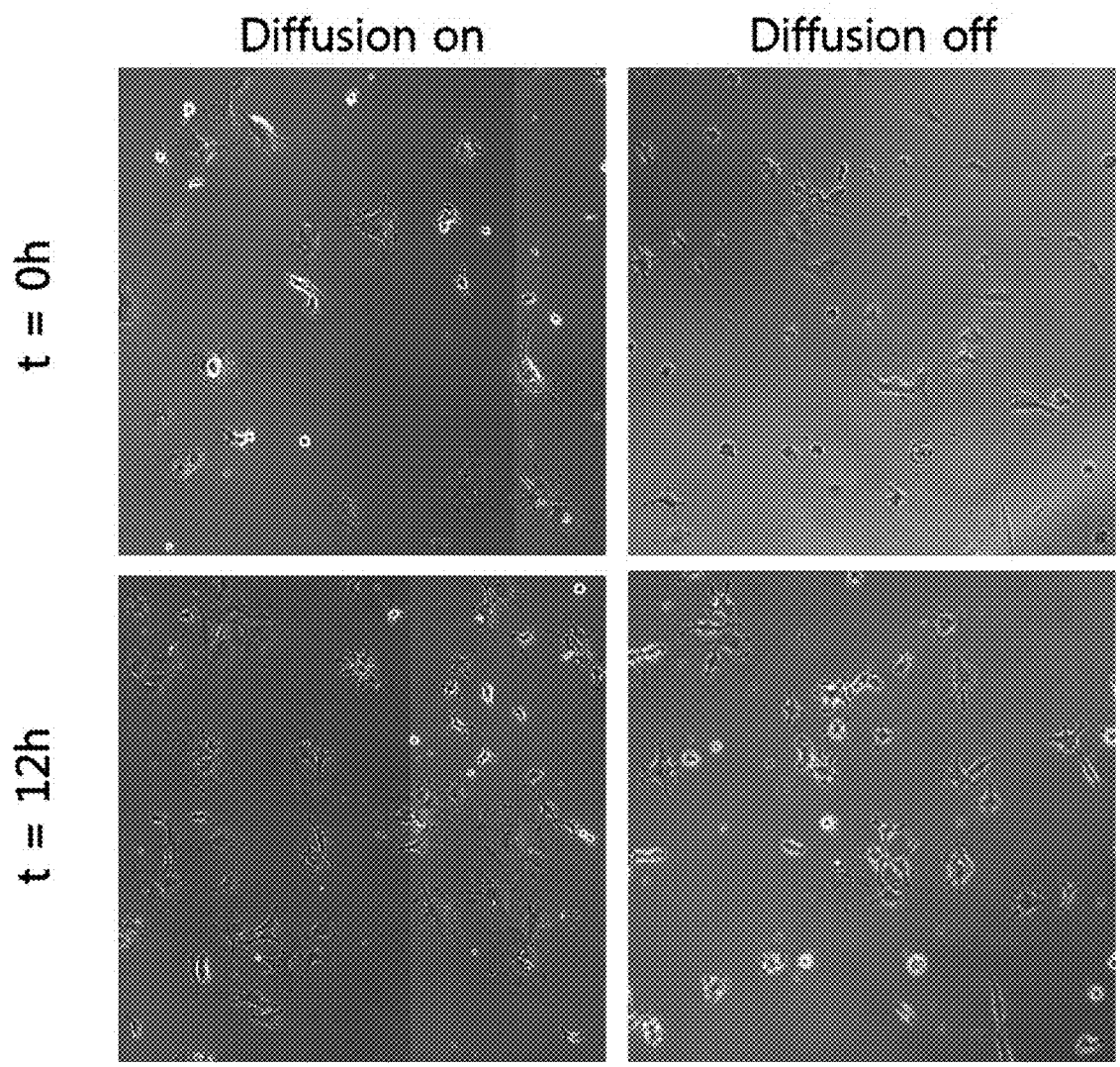
FIGS. 10A and 10B show the photographs of endothelial cells proliferated in two side diffusion chambers 210, 220, respectively, when fluid flow was interrupted (diffusion on) or generated (diffusion off) inside the channels (FIG. 10A) and the proliferation ratio of the endothelial cells (FIG. 10B) in an experiment conducted to investigate whether an in-vivo microenvironment can be controlled with time by culturing the cells in a microfluidic device according to an aspect of the present disclosure.

The proliferation of the endothelial cells was measured as follows. After designating three regions of first and second side diffusion chambers 210, 220 for observation of cellular proliferation, microscopic images were obtained using a phase-contrast microscope (Zeiss, Axio Observer 7) immediately before generating fluid flow in the first or second channel (diffusion switch off) and at 6 hours and 12 hours after generating fluid flow. The result is shown in FIG. 10A. The number of the cells in the images was counted using the ImageJ image analysis program developed by NIH. The images of the cells were converted into binary images to distinguish the cells from the background, and the region where the cells were densely populated was distinguished along the boundary using the watershed algorithm. Only the regions of 50 pixel^2 or higher were counted to exclude noise pixels. The result is shown in FIG. 10B.

Figure 10B:
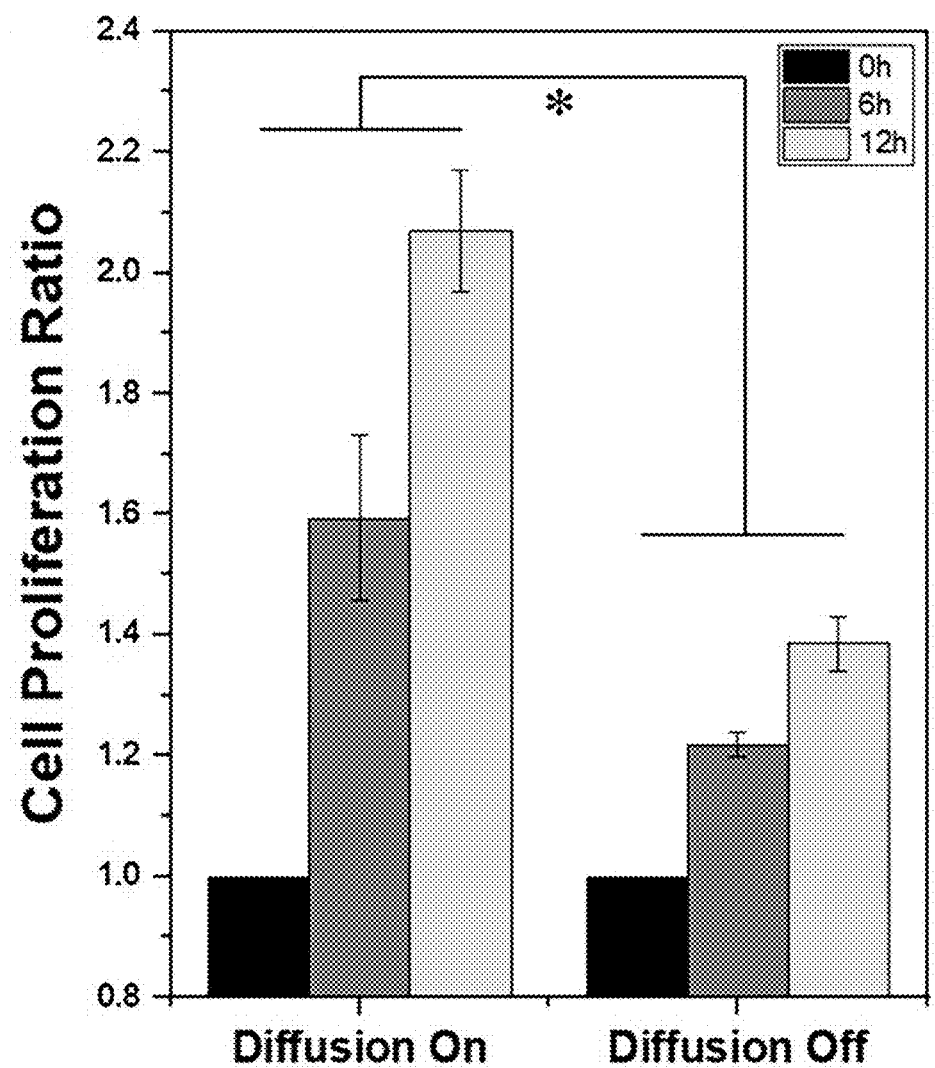

As shown in FIGS. 10A and 10B, the proliferation ratio of the endothelial cells with time was not high for the second side diffusion chamber 220 at the second channel 420 side where fluid flow was generated (diffusion switch off), whereas the proliferation ratio of the endothelial cells was increased very quickly with time for the first side diffusion chamber 210 at the first channel 410 side where fluid flow was interrupted (diffusion switch on). This suggests that the control (switching) of angiogenic response to be achieved in this test example can be determined by the behavior, i.e., proliferation and migration of the endothelial cells (HUVEC) (D. Ribatti, B. Nico, E. Crivellato, A. M. Roccaro, and A. Vacca, "The history of the angiogenic switch concept," *Leukemia*, vol. 21, no. 1, pp. 44-52, 2007). That is to say, it can be seen that, when the diffusion switch is turned on as fluid flow is interrupted, the growth of the endothelial cells (HUVEC) present in the side diffusion chambers is stimulated as the proangiogenic factor VEGF present in the central diffusion chamber 300 is diffused to the side diffusion chambers. Whereas the proliferation ratio of the endothelial cells (ratio of the number of cells after inflow of fluid to the number of cells before inflow of fluid (0 h)) in the second side diffusion chamber 220 at the second channel 420 side was 2.07 at 12 hours after the fluid inflow, the proliferation ratio of the endothelial cells in the first side diffusion chamber 210 at the first channel 410 at the same time was 1.39, which was 1.50 times lower.

Through this, it was confirmed that the diffusion of VEGF from the central diffusion chamber to the side diffusion chambers can be controlled by generating or interrupting fluid flow and the proliferation of cells can also be controlled thereby. Furthermore, it was confirmed that, because the microfluidic device according to an aspect of the present disclosure can turn on/off angiogenic response simply by generating or interrupting fluid flow mechanically, it can mimic the biological microenvironment constantly changing with time by controlling the in-vivo microenvironment such as a tumor microenvironment with time.

[Test Example 3] Confirmation of Controlling of Cell Migration with Time Using Diffusion Switching Mechanism It was confirmed whether an in-vivo microenvironment can be controlled with time by culturing cells in the microfluidic device manufactured in Example 2 and comparing the degree of cell migration.

Figure 11A:
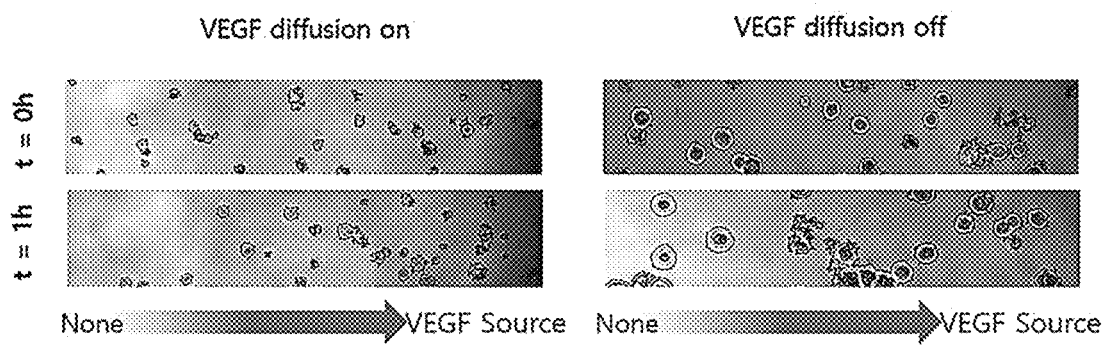
FIGS. 11A and 11B show the photographs showing the migration of endothelial cells in two side diffusion chambers 210, 220, respectively, when fluid flow was interrupted (diffusion on) or generated (diffusion off) in the channels (FIG. 11a) and the degree of migration (CMI) of the endothelial cells (FIG. 11B) in a cell migration experiment conducted to investigate whether an in-vivo microenvironment can be controlled with time by culturing the cells in a microfluidic device according to an aspect of the present disclosure.
Figure 11B:
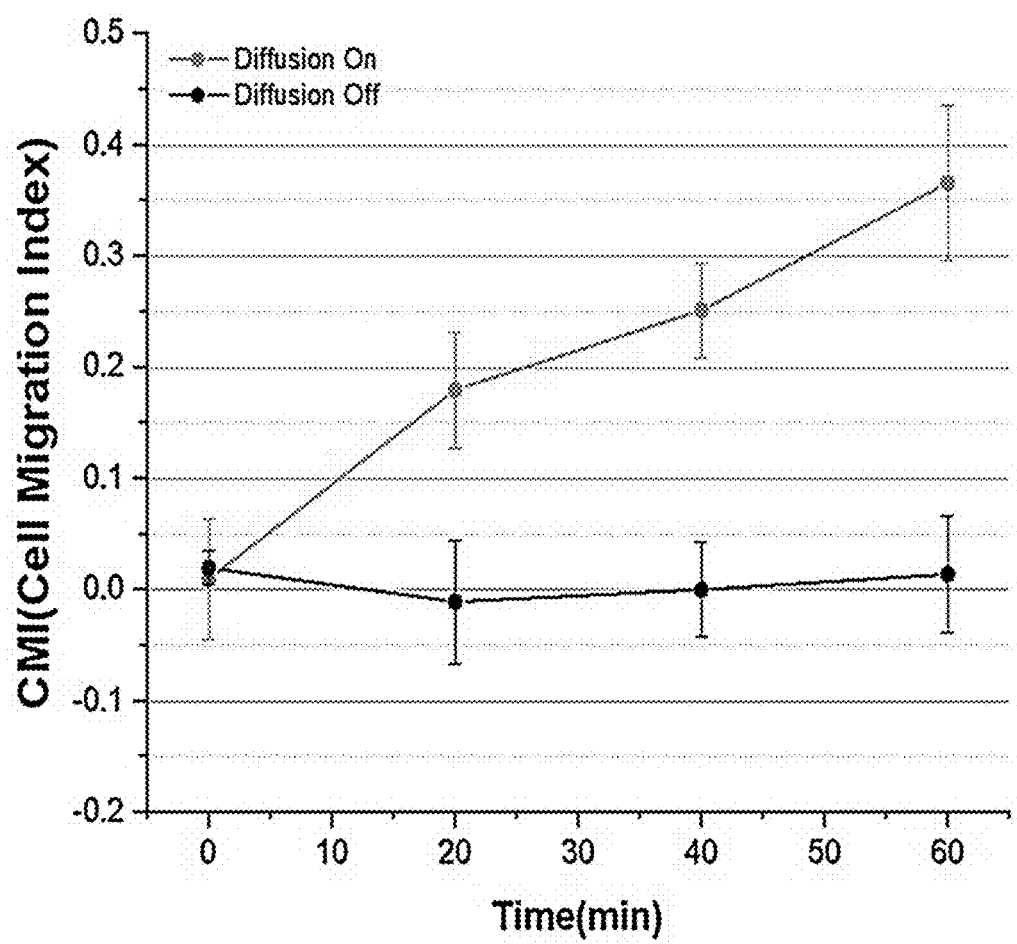
Figure 12A:
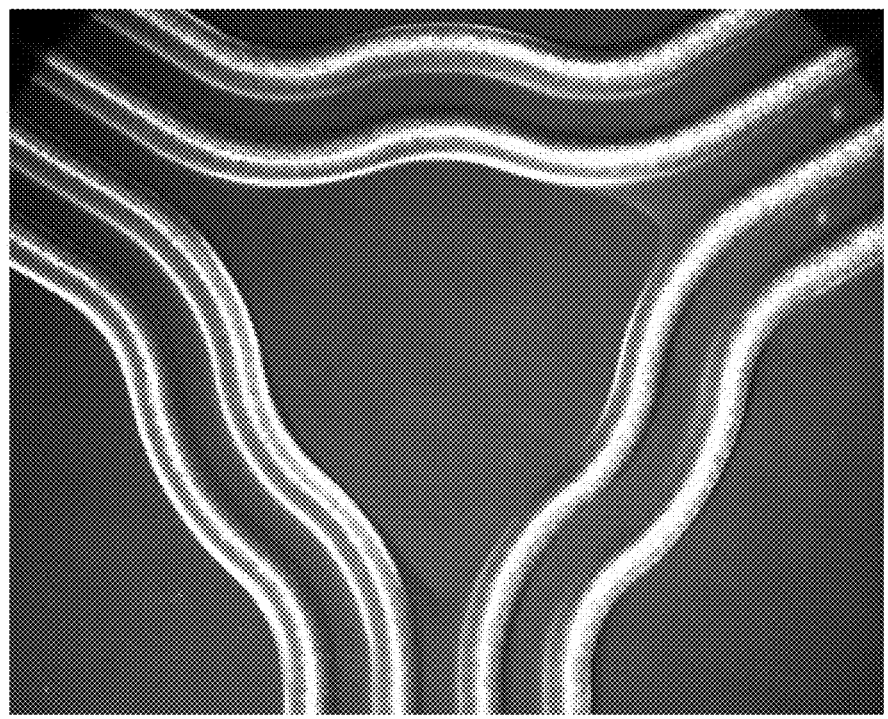
FIGS. 12A and 12B show examples of a microfluidic device according to an aspect of the present disclosure in which the number or shape of diffusion chambers or the number or shape of channels can be changed variously.
Figure 12B:
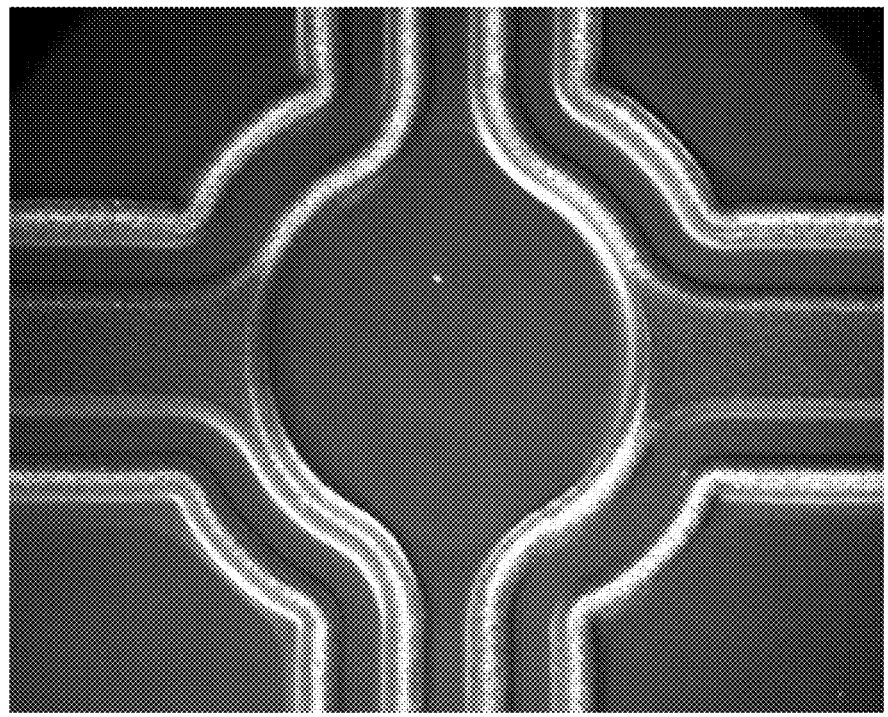

Specifically, the experiment was performed in the same manner as in Test Example 2. The endothelial cells (HUVEC) seeded into the side diffusion chambers 210, 220 were suspended in PBS to expose the endothelial cells to a nutritionally deficient environment in order to facilitate cell migration and the degree of cell migration was compared with cell migration indices (CMI). The result is shown in FIGS. 11A and 11B. The cell migration index is a value calculated from Formula 1, which is a modification of a chemotaxis partition coefficient (CPC) representing the direction of cell migration under a favorable condition, and means the ratio of the endothelial cells present in an unfavorable side ($N_f$) and a favorable side ($N_u$), respectively.

$$CMI = \frac{N_f - N_u}{N_f + N_u}$$ [Formula 1]

In this migration experiment, the endothelial cells (HUVEC) have the tendency to migrate from the central diffusion chamber 300 to the region where VEGF is present in order to obtain nutrients. In this case, a larger CMI value is obtained.

As shown in FIGS. 11A and 11B, for the second channel 420 wherein fluid flow was generated (diffusion switch off), significant migration of the endothelial cells loaded in the second channel 420 to the second side diffusion chamber 220 at the second channel 420 side was not observed (FIG. 11A), because there was no interaction between the central diffusion chamber 300 wherein VEGF was present at a higher concentration and the second side diffusion chamber 220 wherein VEGF was present at a lower concentration. As a result, the CMI value was maintained at about 0 with time (FIG. 11B). In contrast, for the first channel 410 wherein fluid flow was interrupted (diffusion switch on), diffusion of VEGF occurred from the central diffusion chamber 300 wherein VEGF was present at a higher concentration to the first side diffusion chamber 210 wherein VEGF was present at a lower concentration. As a result, in the first side diffusion chamber 210 at the first channel 410 side, the region closer to the central diffusion chamber 300 becomes a favorable side for the endothelial cells, and the region farther from the central diffusion chamber 300 becomes an unfavorable side. Consequently, the endothelial cells loaded in the first side diffusion chamber 210 at the first channel 410 side have the tendency to migrate from the unfavorable side to the favorable side (FIG. 11A) and, as a result, the CMI value was increased from 0.010 to 0.366 within 1 hour after the generation of fluid flow (i.e., 68% of the total population of the endothelial cells migrated to the favorable side), It was also confirmed that, while the fluid flow was interrupted (diffusion switch on), the CMI value maintained a positive value and increased gradually (FIG. 11B).

Through this, it was confirmed that the migration of cells can be controlled through diffusion control of a target element from the central diffusion chamber 300 to the first and second side diffusion chambers 210, 220 by generating or interrupting fluid flow. Therefore, it was confirmed that the microfluidic device according to an aspect of the present disclosure can embody a biological microenvironment such as a tumor microenvironment, which changes constantly with time, via a temporary manipulation of simply generating or interrupting fluid flow in the channel.

The microfluidic device according to an aspect of the present disclosure can mimic the biological microenvironment which changes constantly with time via a simple temporary operation of generating or interrupting fluid flow in the channel mechanically and can control diffusion via a simple method. Therefore, a complicated microenvironment can be reproduced since the number and arrangement of diffusion chambers and channels can be designed variously. Accordingly, the microfluidic device according to an aspect of the present disclosure can be utilized as a powerful tool for performing various biological evaluations in the field of medicine and biology.

| [Detailed Description of Main Elements] | |
|---|---|
| 100: microfluidic device | |
| 210: first side diffusion chamber, | 220: second side diffusion chamber |
| 300: central diffusion chamber | |
| 410: first channel, | 420: second channel |
| 510: first inlet, | 520: second inlet |
| 610: first outlet, | 620: second outlet |
| 700: supporting member | |
| 811: first porous wall, | 812: second porous wall, |
| 821: third porous wall, | 822: fourth porous wall |

What is claimed is:

1. A microfluidic device mimicking a biological microenvironment, comprising:
 a plurality of diffusion chambers including a central diffusion chamber, a first side diffusion chamber, and a second side diffusion chamber; and
 a plurality of channels including a first channel and a second channel,
 wherein the central diffusion chamber extends in a first direction and has a convex shape at a center portion thereof in a plan view,
 the first channel is disposed between the first side diffusion chamber and the central diffusion chamber in the plan view,
 the second channel is disposed between the second side diffusion chamber and the central diffusion chamber in the plan view, and
 the second side diffusion chamber is disposed opposite to the first side diffusion chamber with respect to the central diffusion chamber in a second direction crossing the first direction in the plan view,
 wherein a width of each of the first side diffusion chamber and the second side diffusion chamber in the second direction near the center portion of the central diffusion chamber is at least five times longer than a width of each of the first channel and the second channel in the second direction near the center portion,
 wherein surfaces of the diffusion chambers and the channels are porous, and
 wherein diffusion of a target element between the plurality of diffusion chambers is controlled by interrupting or generating fluid flow inside at least one of the channels.

2. The microfluidic device mimicking a biological microenvironment according to claim 1,
 wherein the microfluidic device further comprises a diffusion control unit, and
 wherein the diffusion control unit comprises: a plurality of inlets through which a fluid is introduced into the plurality of channels, respectively; and a plurality of outlets through which the introduced fluid is discharged.

3. The microfluidic device mimicking a biological microenvironment according to claim 1, wherein a biological sample is loaded in the plurality of diffusion chambers, and the biological sample comprised in each of the plurality of diffusion chambers has a different concentration of the target element.

4. The microfluidic device mimicking a biological microenvironment according to claim 3, wherein the biological sample is one or more selected from a group consisting of a body fluid isolated from an individual, a culture fluid, a growth factor and a cytokine.

5. The microfluidic device mimicking a biological microenvironment according to claim 1, wherein the target element is one or more selected from a group consisting of a cell, a growth factor, a chemokine, a cytokine, a hypoxia-inducible factor and an antibody.

6. The microfluidic device mimicking a biological microenvironment according to claim 5, wherein the cell is one or more selected from a group consisting of a cancer cell, an immune cell, a fibroblast, an endothelial cell and an epithelial cell.

7. The microfluidic device mimicking a biological microenvironment according to claim 1, wherein the control of the diffusion of the target element is achieved as the diffusion of the target element between the plurality of diffusion chambers is interrupted when fluid flow is generated inside at least one of the channel and the diffusion of the target element occurs between the plurality of diffusion chambers when the fluid flow is interrupted inside at least one of the channel.

8. The microfluidic device mimicking a biological microenvironment according to claim 1, wherein the diffusion of the target element is achieved through pores on the surfaces of the diffusion chambers and the channels.

9. The microfluidic device mimicking a biological microenvironment according to claim 1, wherein the surfaces of the plurality of diffusion chambers have a pore size of 5-50 μm.

10. The microfluidic device mimicking a biological microenvironment according to claim 1, wherein the surfaces of the channels have a pore size of 5-50 μm.

11. The microfluidic device mimicking a biological microenvironment according to claim 1, wherein the microfluidic device comprises a porous substrate, and the plurality of diffusion chambers and the plurality of channels are present on the porous substrate.

12. The microfluidic device mimicking a biological microenvironment according to claim 1, wherein one or more of the plurality of diffusion chambers comprises a supporting member therein.

13. A method for manufacturing the microfluidic device mimicking a biological microenvironment according to claim 1, comprising:
 preparing a device-forming solution comprising a prepolymer;
 forming a substrate by coating a scaffold solution comprising a polymer on a plate and forming a cavity in the substrate; and forming a microfluidic device by injecting the device-forming solution into the cavity formed in the substrate and curing the same.

14. A method for controlling a microenvironment in real time, comprising:
interrupting or generating the fluid flow inside the at least one of the channels of the microfluidic device mimicking a biological microenvironment according to claim 1.

15. The method for controlling a microenvironment in real time according to claim 14, wherein the interruption of the fluid flow is achieved by discharging all the fluid present inside the at least one of the channel so that no fluid is present inside the at least one of the channels, and
wherein the generation of the fluid flow is achieved by injecting a fluid into the at least one of the channels so that the fluid is present inside the at least one of the channels.

16. The method for controlling a microenvironment in real time according to claim 14, wherein the diffusion of the target element between the plurality of diffusion chambers is controlled with the interruption or generation of the fluid flow.

17. A method for measuring and observing cellular response using a microfluidic device, comprising:
loading a biological sample in at least one of the diffusion chambers of the microfluidic device mimicking a biological microenvironment according to claim 1; and
interrupting or generating the fluid flow inside the at least one of the channels.

* * * * *